(12) United States Patent
Shen

(10) Patent No.: US 7,345,069 B2
(45) Date of Patent: Mar. 18, 2008

(54) OXIDATIVE ACTIVATION AND EPISULFONIUM ION-MEDIATED DNA ALKYLATION-BASED ANTICANCER

(75) Inventor: Ben Shen, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/097,972

(22) Filed: Apr. 1, 2005

(65) Prior Publication Data

US 2005/0277684 A1    Dec. 15, 2005

Related U.S. Application Data

(60) Provisional application No. 60/558,942, filed on Apr. 2, 2004.

(51) Int. Cl.
C07D 513/08 (2006.01)
A61K 31/381 (2006.01)
(52) U.S. Cl. ........................ 514/368; 540/456
(58) Field of Classification Search ................ 514/368; 540/456
See application file for complete search history.

(56) References Cited

U.S. PATENT DOCUMENTS

| 4,551,433 A | 11/1985 | DeBoer | 435/253 |
| 2003/0175888 A1 | 9/2003 | Shen et al. | 435/69.1 |
| 2003/0216298 A1 | 11/2003 | Gengrinovitch | 514/8 |

FOREIGN PATENT DOCUMENTS

WO    WO 02/077179    10/2002

OTHER PUBLICATIONS

Bierman et al., "Plasmid cloning vectors for the conjugal transfer of DNA from Escherichia coli to Streptomyces spp,"*Gene*, 116(1):43-49, 1992.
Breydo et al., "Two (E,E)- and (Z,E)-thiazol-5-yl-penta-2,4-dienones," *Acta. Cryst.*, C58:447-449, 2002.
Bulseco, "Leinamycin," http://ep.llnl.gov/msds/orgchem/Chem227/leinamycin.html, Found on the internet as early as Mar. 29, 2004.
Cheng et al., "Identification and localization of the gene cluster encoding biosynthesis of the antitumor macrolactam leinamycin in *streptomyces atroolivaceus* S-140," *J. Bacteriol.*, 184(13):7013-7024, 2002.
Cheng et al., "Type I polyketide synthase requiring a discrete acyltransferase for polyketide biosynthesis," *Proc. Natl. Acad. Sci. USA*, 100(6):3149-3154, 2003.
Czerwinski et al., "Cytotoxic agents directed to peptide hormone receptors: defining the requirements for a successful drug," *Proc. Nat'l. Acad. Sci. USA*, 95:11520-11525, 1998.
Froidevaux and Eberle, "Somatostatin analogs and radiopeptides in cancer therapy," *Biopolymers.*, 66(3):161-183, 2002.
Fukuyama et al., "Total Synthesis of (+)-Leinamycin." Ho:YAG laser coronary angioplasty, *J. Synth. Or. Chem., Japan*, 52:888-889, 1994.

GenBank Accession No. AF484556.
Grimm et al., "Characterization of the Streptomyces peucetius ATCC 29050 genes encoding doxorubicin polyketide synthase," *Gene*, 151(1-2):1-10, 1994.
Guilfoile and Hutchinson, "A bacterial analog of the mdr gene of mammalian tumor cells is present in Streptomyces peucetius, the producer of daunorubicin and doxorubicin.," *Proc. Natl Acad. Sci. USA*, 88:8553-8557, 1991.
Hopwood et al., *Genetic Manipulation of Streptomyces: A Laboratory Manual.*, John Innes Foundation: Norwich, UK, 1985.
Hopwood et al., "Plasmid and phage vectors for gene cloning and analysis in Streptomyces," *Meth. Enzymol.*, 153:116-166, 1987.
Huang et al., "Large DNA fragment sizing by flow cytometry: application to the characterization of P1 artificial chromosome (PAC) clones," *Nucl. Acids Res.*, 24:4202-4209, 1996.
Kanda et al., "Synthesis and antitumor activity of leinamycin derivatives: modifications of C-* hydroxy and C-9 keto groups," *Bioorg. Med. Chem. Lett.*, 8:909-912, 1998.
Kao et al., "Engineered biosysnthesis of a complete macrolactone in a heterologous host," *Science*, 265:509-512, 1994.
Kim et al., "Synthesis of thiazole derivatives via Lewis acid promoted reactions of diazopyruvate with thioamides," *Bull. Korean. Chem. Soc.*, 16:4-5, 1995.
Liu and Shen, "Genes for production of the enediyne antitumor antibiotic C-1027 in Streptomyces globisporus are clustered with the cagA gene that encodes the C-1027 apoprotein," *Antimicrob. Agents Chemother.*, 44:382-392, 2000.
Liu et al. "Biosynthesis of the enediyne antitumor antibiotic C-1027," *Science*, 297:1170-1173, 2002.
Motamedi and Hutchinson, "Cloning and heterologous expression of a gene cluster for the biosynthesis of tetracenomycin C, the anthracycline antitumor antibiotic of Streptomyces glaucescens, " *Proc. Nat'l Acad. Sci. USA*, 84:4445-4449, 1987.
Osoegawa et al., "An improved approach for construction of bacterial artificial chromosone libraries," *Genomics*, 52(1):1-8, 1998.
Pieper et al., "Remarkably broad substrate specificity of a modular polyketide synthase in a cell-free system, " *J. Am. Chem. Soc.*, 117(45):11373-11374, 1995.
Pieper et al., "Cell-free synthesis of polyketides by recombinant erythromycin polyketide synthases," *Nature*, 378(6554):263-266, 1995.
Roy et al., "Thiazole and oxazole peptides: biosynthesis and molecular machinery," *Nat. Prod. Rep.*, 16;249-263, 1999.
Shen and Hutchinson, "Triple hydroxylation of tetracenomycin A2 to tetracenomycin C in Streptomyces glaucescens. Overexpression of the tcmG gene in Streptomyces lividans and characterization of the tetracenomycin A2 oxygenase," *J. Biol. Chem.*, 269:30726-30733, 1994.

(Continued)

Primary Examiner—Bruck Kifle
(74) Attorney, Agent, or Firm—Fulbright & Jaworski L.L.P.

(57) ABSTRACT

The present invention relates to TG-25 and/or analogs thereof and their use of TG-25 in the treatment of cancer. TG-25 inhibits the growth of prostate cells by inhibiting DNA synthesis, more particularly by DNA cleavage.

2 Claims, 12 Drawing Sheets

OTHER PUBLICATIONS

Smith et al., "Genetic localization and molecular characterization of the nonS gene required for macrotetrolide biosynthesis in Streptomyces griseus DSM40695," *Antimicrob. Agents Chemother.*, 44:1809-1817, 2000.

Stutzman-Engwall and Hutchinson, "Multigene families for anthracycline antibiotic production in Streptomyces peucetius," *Proc. Nat'l. Acad. Sci. USA*, 86:3135-3139, 1989.

Tang et al., Leinamycin biosynthesis revealing unprecedented architectural complexity for a hybrid polyketide synthase and nonribosomal peptide synthetase, *Chemistry & Biology*, 11:33-45, 2004.

Vara et al., "Cloning of genes governing the deoxusugar portion of the erythromycin biosynthesis pathway in Saccharopoly erythraea (Streptomyces erythreus)," *J. Bacteriol.*, 171:5872-5881, 1989.

Wang et al., "GroEL-GroES-mediated protein folding requires an intact central cavity," *Proc. Nat'l. Acad. Sci. USA*, 95:12163-12168, 1998.

Wiesmann et al., "Polyketide synthesis in vitro on a modular polyketide synthase," *Chem. & Biol.*, 2(9):583-589, 1995.

Woon et al., "Construction and characterization of a 10-fold genome equivalent rat P1-derived artifical chromosome library," *Genomics*, 50:306-316, 1998.

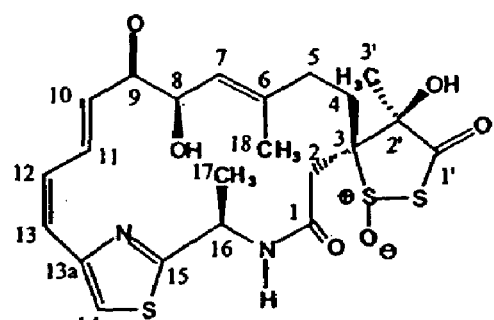
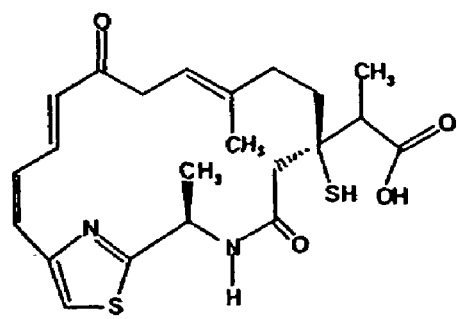
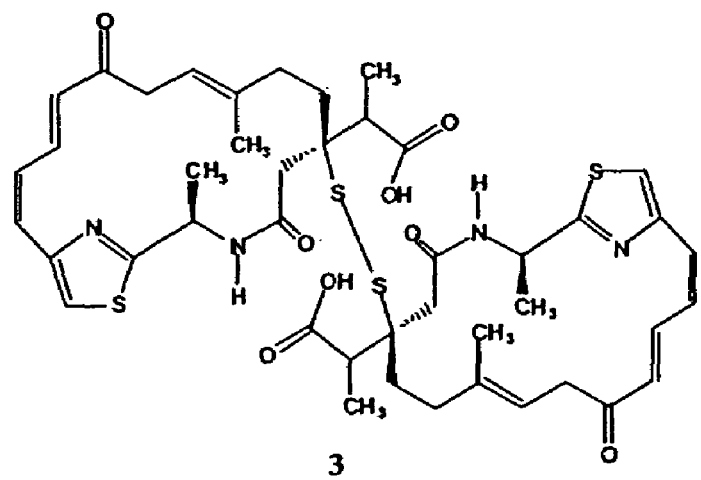
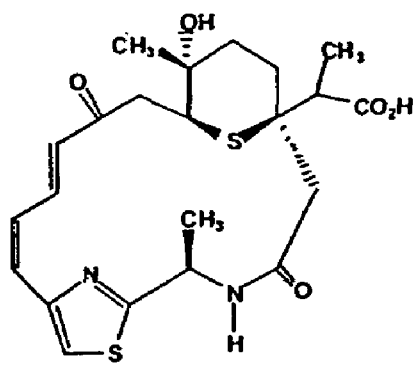
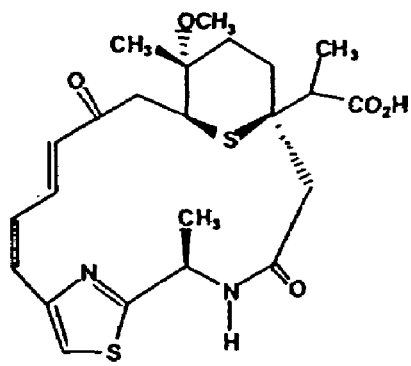
FIG. 5

OXIDATIVE ACTIVATION AND EPISULFONIUM ION-MEDIATED DNA ALKYLATION-BASED ANTICANCER

This application claims the priority of U.S. Provisional Application Ser. No. 60/558,942, filed Apr. 2, 2004, the entire contents of which are hereby incorporated by reference. This invention was made with government support under grant CA094426 awarded by the National Institute of Health. The government has certain rights in the invention.

TECHNICAL FIELD

The present invention relates generally to the fields of cancer biology and cancer therapeutics. More particularly, it concerns the use of TG-25, and analogs thereof, in the treatment of prostate cancer.

BACKGROUND OF THE INVENTION

Prostate cancer is the most commonly diagnosed malignancy in United States males, and is the second leading cause of male cancer deaths in the U.S. (Feuer et al., 1999). As medical care and overall health lead to increases in the age of the male population, so too will the incidence of prostate cancer. As such, the prevention of prostate cancer is of national medical concern. While surgery, radiotherapy and androgen ablation therapy of prostate cancer is available for the treatment of the disease at an early stage, no effective therapy is currently available against the advanced metastatic disease.

Antitumor antibiotics have been the focus of recent cancer research. Most of these antibiotics kill cells by interacting with cellular DNA inducing DNA cross-linking and strand breaks, as well as by activiating cellular apoptotic machinery. Recently, a new antitumor antibiotic, leinamycin (LNM) has shown potency in various murine tumor models. LNM exerts its cytoxicity by a thio-dependent, alkylative DNA cleavage mediated by an episulfonium ion intermediate. Although LNM appears to be more effective at killing tumor cells, the mode of activation for LNM requires a reductive environment.

While most cancer cells are under hypoxic conditions (ideal for reductive activation), prostate cancer cells are unique in such that they are under high oxidative stress. The oxidative environment of prostate cancer cells might be one of the reasons that renders clinically important anticancer drugs that require reductive active activation ineffective. Thus, in view of the oxidative environment of prostate cancer cells, the generation of LNM antibiotics may not be as effective, thus, there is still a need for an effective antitumor antibiotic to treat prostate cancer.

BRIEF SUMMARY OF THE INVENTION

An embodiment of the present invention is a compound (referred to herein as "TG-25 compound") having the structure:

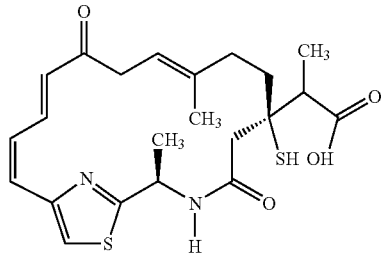

or an analog thereof.

One embodiment of the present invention comprises a method of inhibiting growth of a cancer cell having an oxidative cellular environment comprising contacting said cell with an effective amount of the compound or an analog thereof. In certain embodiments, the cancer cell is a prostate cancer cell. In further embodiments, the analog has one or more of the following modifications, for example, variations at the carboxy group resulting in the production of esters and amides or variations of the thiol group resulting in a thioester or dithiol.

Another embodiment is that the cancer cell is a drug-resistant cancer cell. The cells may be contacted by providing the compound or an analog thereof to the cell and/or a prodrug to the cell, which is converted in situ to TG-25 compound or an analog thereof. An effective amount may comprise about 0.1 µM to about 100 µM. Yet further, the present invention comprises contacting the cell with a second agent, for example, but not limited to a radiation, chemotherapeutic, an inhibitor of DNA repair, for example, etoposide (VP16), an agent that promotes an oxidative environment in the cell, a steroid (i.e., a natural or synthetic androgen or analog thereof), or a biological anti-cancer agent (i.e., an antibody, an antisense molecule, an siRNA, a tumor suppressor, a pro-apoptotic protein, a cell cycle regulator, a cytokine, or an expression construct encoding any of the foregoing).

Another embodiment of the present invention is a method of treating cancer in a subject, wherein said cancer is characterized by cells having an oxidative cellular environment, comprising contacting the subject with an effective amount of a TG-25 compound or analogs thereof. The cancer cell may be a prostate cancer cell, a primary cancer cell or a metastatic cancer cell. More specifically, the subject may suffer from recurrent prostate cancer. The subject may be administered the compound, prodrug or analog orally, intravenously, intraarterially or intratumorally. In further embodiments, the subject may be contacted with said compound or analog thereof more than once. Yet further, the cell may be contacted with a second agent.

Another embodiment of the present invention there is provided a bacterial host cell that produces a TG-25 compound or analog thereof. In preferred embodiments, the host cell is a Streptomyces cell, more specifically, a Streptomyces atroolivaceus cell. Still further, the host cell is designated as Streptomyces atroolivaceus-lnmE. More specifically, the Streptomyces atroolivaceus cell comprises a mutated lnmE gene. The lnmE may be mutated by site-directed mutagenesis, gene replacement, or gene disruption. In certain embodiments, the lnmE gene is mutated by replacing a portion of the lnmE gene with an acc(3)IV apramycin-resistant gene.

Another embodiment of the present invention is a pharmaceutical composition comprising a TG-25 compound or an analog thereof, dispersed in a pharmaceutical buffer diluent or carrier. Yet further, the pharmaceutical composition can comprise an agent that promotes an oxidative environment in cells.

Still yet, another embodiment of the present invention is a method of screening for an agent toxic to cancer cells comprising: (a) providing a cell having an oxidative environment; (b) selecting a candidate substance that comprises one or more substituents that are subject to oxidative reaction; (c) contacting said candidate substance with said cell; and (d) assessing the toxicity of said candidate substance on said cell, wherein toxicity to said cell in the presence of said candidate substance, as compared to that observed in the absence of said candidate substance, indicates that said candidate substance is an agent toxic to cancer cells. Yet further, the method comprises assessing the toxicity of said candidate substance on a cell having a reductive environment.

It is contemplated that any method or composition described herein can be implemented with respect to any other method or composition described herein.

In embodiments, the cell is treated with a second agent prior to step (c), wherein said second agent promotes an oxidative environment in said cell. In further embodiments, a second agent can be a natural or synthetic androgen or derivative thereof.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows reductive activation by RSH for LNM. FIG. 1B shoes oxidative activation by $O_2$ for TG-25.

FIG. 2A shows modification at the COOH group. FIG. 2B shows modifications at the thiol group.

FIG. 5 shows structures of compounds 2, 3, 4, and 5 isolated from the ΔlnmE mutant.

DETAILED DESCRIPTION OF THE INVENTION

Figure 1:
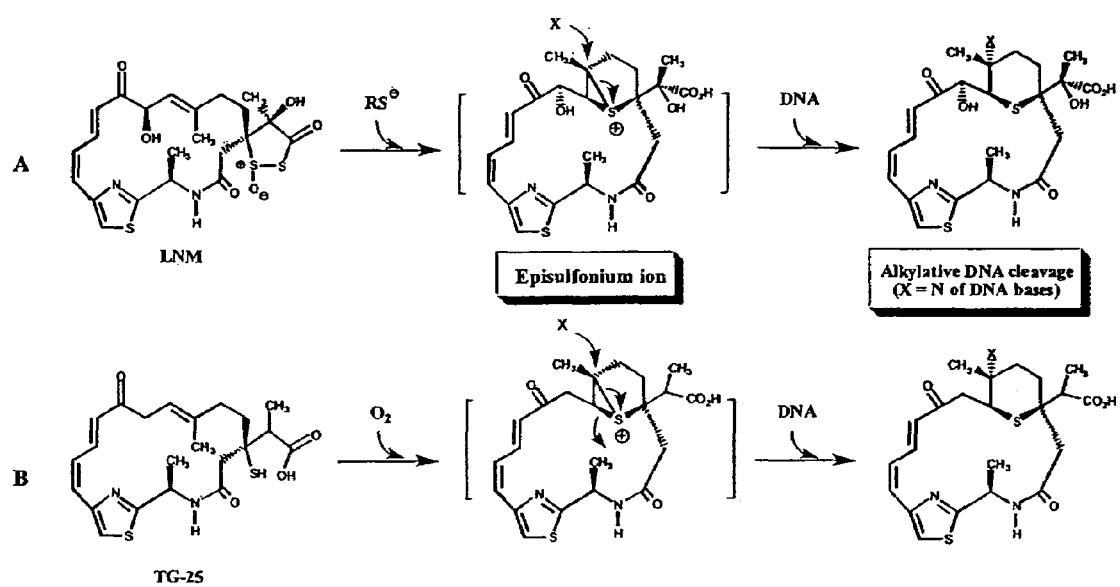
FIG. 1A and FIG. 1B show the mode of action for LNM and TG-25 as anticancer drugs mediated by episulfonium ion intermediates.

It is readily apparent to one skilled in the art that various embodiments and modifications can be made to the invention disclosed in this Application without departing from the scope and spirit of the invention.

Present Invention

Advanced hormone refractory metastatic prostate cancer is the second leading cause of cancer deaths among U.S. men. It is estimated that about 30,000 men will die of this disease in the course of this year. While surgery, radiotherapy and androgen ablation therapy of prostate cancer are available for the treatment of the disease at an early stage, no effective therapy is currently available against the advanced metastatic disease. Most commonly used anticancer agents have shown only limited success in the treatment of metastatic prostate cancer. Development of novel chemotherapeutic agents effective against advanced prostate cancer is urgently needed.

Since the oxidative environment of prostate cancer cells might be one of the reasons that renders clinically important anticancer drugs that require reductive activation ineffective, it is reasonable to conclude that prostate cancer cells should be susceptible to oxidatively activated agents such as TG-25.

A *Streptomyces atroolivaceus* recombinant strain was engineered to specifically produce a novel leinamycin analog TG-25 that generates an episulfonium ion intermediate to kill cancer cells by alyklative DNA cleavage which is activated in an oxidative environment. TG-25 inhibits the growth of LNCaP prostate cancer cells, pretreated with 1 nM androgen analog R1881, with an $IC_{50}$ at 5–10 μM. Co-pretreatment of the LNCaP prostate cancer cells with R1881 and vitamin E completely reverses the growth inhibitory effect. TG-25 therefore represents a novel anticancer drug lead against prostate cancer by an unprecedented mode of action via in situ oxidative activation and episulfornium ion-mediated alyklative DNA cleavage. Thus, this invention describes the production of TG-25 and analogs thereof and their use as an anti-prostate cancer agents.

TG25 and Analogs

In certain embodiments, TG-25 having the below structure, is produced using the ΔlnmE mutant strain of *S. atroolivaceus*.

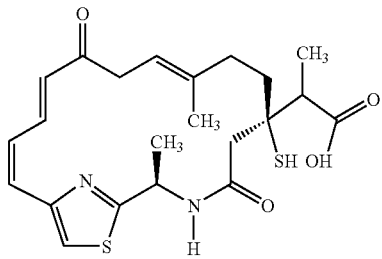

Other metabolites similar to the structure of TG-25 having a similar function such as production of episulfornium ion intermediates under an oxidative environment are also envisioned in the present invention. As one of skill in the art understands, these metabolites can be synthesized utilizing standard organic synthesis methods and/or combinatorial biosynthesis. The structural complexity of metabolites such as TG-25 is a challenge for organic synthesis to prepare them in significant amounts for pre-clinical and clinical investigations. An alternative to organic synthesis is combinatorial biosynthesis, which is manipulation of the microbial genes that govern the biosynthesis of complex natural products and their analogs. For example, structural alterations in the presence of other functional groups can be achieved and the target molecules can be produced by recombinant organisms that are amendable to large-scale fermentation.

Synthesis

In certain embodiments of this invention, the LNM biosynthetic gene cluster is modified so as to introduce variations into the gene cluster to produce TG-25 analogs, which is a novel analog of LNM, as described in detail in Example 2. Such variation may be introduced by design, for example to modify a known molecule in a specific way, e.g., by replacing a single monomeric unit within a polymer with another, thereby creating a derivative molecule of predicted structure. Alternatively, variations can be made randomly, for example by making a library of molecular variants of a known polymer by systematically or haphazardly replacing one or more modules or enzymatic domains.

Cloning, for example, but not limited to targeted gene disruption, gene overexpression and/or gene replacement in *Streptomyces* can be used in the present invention. Methods of cloning and expressing large nucleic acids such as gene clusters, in cells including *Streptomyces* are well known to those of skill in the art (Stutzman-Engwall and Hutchinson, 1989; Motamedi and Hutchinson, 1987; Grim et al., 1994; Kao et al., 1994; and Hopwood et al., 1987). In some examples, nucleic acid sequences of well over 100 kb have been introduced into cells, including prokaryotic cells, using vector-based methods (see, for example, Osoegawa et al., 1998; Woon et al., 1998; Huang et al., 1996).

A wide variety of expression vectors and host cells are suitable for the synthesis of leinamycin analogs, more specifically TG-25 and analogs thereof. The choice of vector depends on the sequence(s) that are to be expressed. Any transducible cloning vector can be used as a cloning vector for the nucleic acid constructs of this invention. However, where large clusters are to be expressed, phagemids, cosmids, P1s, YACs, BACs, PACs, HACs or similar cloning vectors can be used for cloning the nucleotide sequences into the host cell. Phagemids, cosmids, and BACs, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., 1989). The utility of employing such vectors having different marker genes may be exploited to facilitate a determination of successful transduction.

In a certain embodiment, *Streptomyces* vectors are used that include sequences that allow their introduction and maintenance in *E. coli*. Such *Streptomyces/E. coli* shuttle vectors have been described (see, for example, Vara et al., 1989; Guilfoile & Hutchinson, 1991).

*S. atroolivaceus* is sensitive to thiostrepton (Thi) and apramycin (Apr). Thus, in one preferred embodiment a vector carrying the $Thi^R$ marker, and a vector, carrying the $Apr^R$ marker, are particularly well suited for expression of lnm nucleic acids. Introduction of plasmid DNA into *S. atroolivaceus* by either polyethyleneglycol (PEG)-mediated transformation of protoplasts (Hopwood et al., 1985) or by conjugation from *E. coli* S17 (Bierman et al., 1992) was successful, demonstrating the feasibility of manipulating Lnm biosynthesis in *S. atroolivaceus* in vivo.

The gene sequences, or fragments thereof, which collectively encode the lnm gene cluster, one or more ORFs, one or more lnm modules, or one or more lnm enzymatic domains, can be inserted into expression vectors, using methods known to those of skill in the art, exemplary methods are described in publications written by Cheng et al., 2002; Tang et al., 2004; and Cheng et al., 2003, which are incorporated herein by reference. Gene sequences which encode the lnm gene cluster are more readily described in U.S. Patent Application No. US20030175888, which is incorporated herein in its entirety, and GenBank accession number for the lnm gene cluster is AF484556. Suitable expression systems for use with the present invention include systems that function in eukaryotic and prokaryotic host cells. However, as explained above, prokaryotic systems are preferred, and in particular, systems compatible with *Streptomyces* spp. are of particular interest. Control elements for use in such systems include promoters, optionally containing operator sequences, and ribosome binding sites. Exemplary promoters include, but are not limited to bacterial promoters, such as those derived from sugar metabolizing enzymes, such as galactose, lactose (lac) and maltose. Additional examples include promoter sequences derived from biosynthetic enzymes such as tryptophan (trp), the beta-lactamase (bla) promoter system, bacteriophage lambda PL, and T5. In addition, synthetic promoters, such as the tac promoter (U.S. Pat. No. 4,551,433, which is incorporated herein by reference in its entirety), which do not occur in nature also function in bacterial host cells. In *Streptomyces*, numerous promoters have been described including constitutive promoters, such as ermE and tcmG (Shen and Hutchinson, 1994), as well as controllable promoters such as actI and actIII (Pleper et al., 1995; Pieper et al., 1995; and Wiesmann et al., 1995).

Other regulatory sequences may also be desirable which allow for regulation of expression of the replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, fore example, enhancer sequences.

Selectable markers can also be included in the recombinant expression vectors. A variety of markers are know which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid. Alternatively, several polyketides are naturally colored and this characteristic provides a built-in marker for selecting cells successfully transformed by the present constructs.

Host cells for the recombinant production of the TG-25 and/or TG-25 analogs, and the like can be derived from any organism with the capability of harboring a recombinant lnm gene cluster. Thus, the host cells of the present invention can be derived from either prokaryotic or eukaryotic organisms. However, preferred host cells are those constructed from the actinomycetes, a class of mycelial bacteria that are abundant producers of a number of polyketides and peptides. A particularly preferred genus for use with the present system is *Streptomyces*. Thus, for example, *S. verticillus S. ambofaciens, S. avermitilis, S. atroolivaceus, S. azureus, S. cinnamonensis, S. coelicolor, S. curacoi, S. erythraeus, S. fradiae, S. galilaeus, S. glaucescens, S. hygroscopicus, S. lividans, S. parvulus, S. peucetius, S. rimosus, S. roseofulvus, S. thermotolerans, S. violaceoruber*, among others, will provide convenient host cells for the subject invention (see, e.g., Hopwood and Sherman, 1990; O'Hagan, D., 1991), for a description of various polyketide-producing organisms and their natural products).

In specific embodiments, gene disruption is preformed which may involve the cloning of an internal fragment of approximately, for example 1–5 kB, from the target gene into a vector and the introduction of the construct into the target *Streptomyces* host. Under conditions that disfavor plasmid replication but favor chromosomal integration via homologous recombination by a single crossover event, *Streptomyces* recombinants will be isolated by selection for the vector marker. The target gene is truncated by the vector in the isolated mutant, resulting in inactivation of the target gene. Alternatively, methods for gene replacement involve the insertion of a detectable marker gene into the target gene so that approximately 1–5 kB of the host DNA flanks the marker gene, followed by the introduction of the construct with the marked gene into the target *Streptomyces* host. Under similar conditions as those for gene disruption, *Streptomyces* recombinants will be isolated by selection first for both the vector marker and the disrupting marker gene (the first crossover event) and then for loss of the vector marker and maintenance of the disrupting marker gene (the second crossover event). The chromosomal target gene is replaced by the disrupted version with the resistance maker gene inserted in the middle of the target gene in the isolated mutant, resulting in an inactivation of the target gene. In vivo complementation by either expressing the native copy of the inactivated gene or supplementing biosynthetic intermediates to restore the wild-type phenotype to the mutant strain should eliminate any concern of polar effect on downstream genes. The exact choice of vector, marker gene, and conditions favoring integration of the initial construct into the chromosome can be determined by those of skill in the art (Cheng et al., 2002; Cheng et al., 2003; Kwon et al., 2002; Liu et al., 2002; Smith et al., 2000; Liu et al., 2000).

Other efficient systems for gene expression in either *E. coli* or *Streptomyces* species can be used in the present invention. For example, the pET (Novagen, Inc., "pET system Mannual" $5^{th}$ Ed., 1995, Madison, Wis.) or pQE (QIAGEN, Inc. "The QIAexpressionist" $3^{rd}$ ED., 1997, Santa Clarita, Calif.). The expression efficiency in *E. coli* for genes from *Streptomyces* can be optimized by specific modification at the third positions of the first a few codons of the target gene, taking into account the biased codon usage of streptomycetes (Gramajo et al., 1991). The solubility of the overproduced proteins can be dramatically improved by either co-expression of chaperonins, such as *E. coli* GroEL/S (Wang et al., 1997) or the combination of low incubation temperature (as low as 17° C.), long incubation time (up to 12 hrs after induction), and low or none IPTG induction. The target gene can be expressed either as the native protein or N- or C-terminal fusion proteins. Various pET or pQE vectors for the latter are available that contain different sequences adjacent to the cloning sites. These sequences encode for a variety of peptide "tags" for detection and purification of the target protein. The peptide tags can facilitate isolation of enzymes if we encounter difficulty in the purification of the native proteins. These tags normally do not interfere with the enzyme activities and can be removed if they do become a problem.

These above methods have been used to genetically manipulate the LNM biosysthsis *S. atroolivaceus* S-140 by gene disruption (ΔlnmI), gene replacement ((ΔlnmI, ΔlnmJ, and ΔlnmG), and gene overexpression (lnmG) (Cheng et al., 2002; Cheng et al., 2003). Yet further, U.S. Patent Application US20030175888, which is incorporated herein in its entirety, provide a further detailed explanation of genetic manipulation of the LNM biosynthetic pathway.

In specific embodiments of the present invention, genetic manipulation of LNM biosynthetic gene cluster resulted in a mutant *S. atroolovaceius* strain, ΔlnmE that produces a novel metabolite TG-25. Yet further, this invention may make use of genetically engineered cells that contain a mutated lnm gene cluster to identify other analogs of metabolites which are activated in an oxidative environment to produce the episulfonium ion. Still further, the invention provides for the production of significant quantities of TG-25 and/or TG-25 analogs to be used as therapeutic agents, to treat prostate cancer.

In addition to the use combinatorial biosynthesis to generate TG-25 and/or its analogs, traditional organic synthesis may be used to generate TG-25 and/or its analogs. Since LNM has been synthesized using traditional organic synthesis, one of skill in the art would be able to utilize similar conditions to organically synthesize TG-25 and/or analogs thereof (Fukuyama and Kanda, 1994; Fukuyama and Kanda, 1994, 1993; Kanda et al., 1998, which are incorporated herein by reference). For example, the starting compound may be a substituted lactone, i.e., 2-methyl, 3-oxo, 4-tert butyl δ lactone, that undergoes suitable reactions to produce functionalized carbon moieties that extend to the penultimate intermediate(s) side chains and through certain cyclization reactions produce compounds whose functional groups may be further reacted to produce the final compound(s). Exemplary reactions included, but are not limited to the use of LDA in a directed aldol reaction, reactions of ketones from lithium dialkylcuprates, electrophilic substitution reactions of aromatic heterocyclic amines, synthesis addition of hydrogen, and synthesis of cis-alkenes.

Modifications to TG-25 and/or Analogs

In still further embodiments, it is contemplated that the TG-25 compound or analog of the present invention may be further modified to comprise a targeting factor, such as a peptide to target a specific tissue and/or cell or transport molecule to transport the compound to specific tissues.

Peptide synthesis may be used to bond peptides to organic molecules to increase the specificity of the organic molecules to the target tissues and/or cells. Exemplary peptides, may include fore example, endothelial penetration peptide (enables the composition to cross through the endothelial barrier), receptor ligands (i.e., ligands directed to hormone receptors; ligands directed to other cell surface receptors), antibody fragments or antibodies, and radiolabeled peptides (see Froidevauz, and Eberle, 2002). Exemplary types of peptides that may be used include, for example, peptides that target the vasculator (i.e., vascular endothelial growth factor (VEGF)/VEGF-receptor complex, alpha(v) integrins, and Tie receptor tyrosine kinases (see Arap et al., 1998; Ellerby et al., 1999), integrin homing domain RGD (see Chen et al., 2001), and NGR-containing peptides (i.e., CNGRC peptide is an aminopeptidase N (CD13) ligand that targets activated blood vessels in tumors) (see Curnis et al., 2000; Curnis et al., 2002).

Synthesis of the TG-25 compound or analog to a peptide may utilize a solid-phase peptide synthesis procedure as described in U.S. Patent Application US20030216298, which is incorporated herein by reference (see also, Czerwinski et al., 1998). In this method, the C-terminal, N-terminal and/or a side chain of the peptide sequence is attached to a cross-linked resin, i.e., polystyrene resin, with a linker molecule. A linker may be any chemical compound present between the TG-25 compound or analog and the peptide which may be removed chemically, enzymatically or may decompose spontaneously. A protection group, i.e., Fmoc group, may also be added to the peptide sequence to protect the N-terminal, the C-terminal and/or a side chain of the sequence. In certain embodiments, the TG-25 compound or analog is bound to a peptide sequence to form a peptide-TG-25 conjugate, in which the peptide sequence further comprises a peptide bond that is specifically cleavable by a protease. A protease specific cleavable sequence may be any peptide sequence which comprises a peptide bond cleavable by a specific protease, which is more abundant within or in proximity to the cancer cells. One of skill in the art realizes that the TG-25 compound or analog may be placed at either the N-terminal or C-terminal side of the peptide. In certain embodiments, once the conjugate enters the cell or upon entering the cell, the TG-25 compound or analog may be cleaved from the peptide sequence and/or the linker.

Another example of targeting TG-25 or its analog to tissues and/or cells includes the use of transport molecules for example, but not limited to cholesterol, lipids, glucose, steroids, etc. Depending on the uptake mechanism targeted, different modifications can be employed. To target passive diffusion, lipid modification may be used, whereas the targeting of sugar transport systems may be used if the TG-25 compound or analog is conjugated with sugars. These types of delivery systems can be specifically tailored to transport a wide variety of poorly absorbed compounds through the skin, and across the barriers that normally inhibit absorption from the gut or into the brain. The delivery system can be conjugated to the compound in such a way as to release the active compound after it has been absorbed or to form a biologically stable and active molecule.

Purification of TG-25 and/or Analogs

Once the metabolites have been synthesized either by organic synthesis and/or combinatorial biosynthesis. Any of a wide variety of chromatographic procedures may be employed according to the present invention. For example, thin layer chromatography, gas chromatography, high performance liquid chromatography, paper chromatography, affinity chromatography or supercritical flow chromatography may be used to effect separation of various chemical species.

Partition chromatography is based on the theory that if two phases are in contact with one another, and if one or both phases constitute a solute, the solute will distribute itself between the two phases. Usually, partition chromatography employs a column, which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography.

Screening to Identify Analogs of TG-25 Other Anticancer Compounds

In a particular embodiment, the present invention provides methods for identifying analogs of the compound TG-25. TG-25 may be used as a target in screening for similar compounds that form episulfonium ion intermediates under oxidative conditions, inhibit DNA synthesis, induce alkylative DNA cleavage, induce cell cycle arrest, inhibit cell growth or induce apoptosis in cells such as cancer cells. Assays may focus on particular classes of compounds selected with an eye towards structural attributes that are believed to make them more likely to mimic the effect of TG-25. In some instances, libraries may be randomly screened for candidate substances. By effect, it is meant that one may assay for formation of episulfonium ion intermediates under oxidative conditions, alkylative DNA cleavage, cell cycle arrest, growth inhibition, or induction of apoptosis in a hyperproliferative cell such as a cancer cell, more specifically for a prostate cancer cell.

To identify a TG-25 analog, one generally will determine the anticancer activity in the presence and absence of the candidate substance, wherein an analog is identified by its ability to formation of episulfonium ion intermediates, cell cycle arrest, induce alkylative DNA cleavage, inhibit DNA synthesis, inhibit cell growth or induce apoptosis in cells such as cancer cells. For example, a method may generally comprise:

(a) providing a cell having an oxidative environment;
(b) selecting a candidate substance that comprises one or more substituents that are subject to oxidative reaction;
(c) contacting the candidate substance with the cell; and
(d) assessing the toxicity of the candidate substance on the cell, wherein toxicity to the cell in the presence of the candidate substance, as compared to that observed in the absence of the candidate substance, indicates that the candidate substance is an agent toxic to prostate cancer cells.

In preferred embodiments, the cell is treated with a second agent prior to step (c), wherein the second agent promotes an oxidative environment in the cell. Such agents that can promote an oxidative environment include, but are not limited to hydrogen peroxide, superoxide radicals, nitric oxide, etc.

In a further aspect of the present invention, the second agent may be, for example, a natural or synthetic androgen or derivative thereof, for example, but not limited to R1881.

Still further, in certain embodiments, the screening method may comprise assessing the toxicity of the candidate substance on a cell having a reductive environment.

Assays may be conducted in isolated cells, or in organisms including animals. It will, of course, be understood that all the screening methods of the present invention are useful in themselves notwithstanding the fact that effective candidates may not be found. These assays may be performed at a lab bench by a human operator, via mechanized high through-put screening, or any other manner known in the art. The candidate substance(s) tested may be an individual candidate or one or more of a library of candidates and may be obtained from any source and in any manner known to those of skill in the art.

As used herein the term "candidate substance" or "candidate compound" refers to any TG-25-related compound that may potentially form episulfonium ion intermediates in an oxidative environment, induce DNA cleavage, for example alkylative DNA cleavage, inhibit DNA synthesis, inhibit the cell cycle, inhibit cell growth or induce apoptosis.

Any compound or molecule described in the methods and compositions herein may be a candidate TG-25 substance or compound.

The TG-25 compound of the present invention may be used in rational drug design to produce structural analogs of biologically active compounds. By creating such analogs, it is possible to fashion drugs which are more active or stable than the natural molecules, which have different susceptibility to alteration or which may affect the function of various other molecules. In one approach, one would generate a three-dimensional structure for the TG-25 compound of the invention or a portion thereof. This could be accomplished by x-ray crystallography, computer modeling or by a combination of both approaches. An alternative approach, involves the random replacement of functional groups throughout the TG-25 compound, and the resulting affect on the function of the analog or derivative determined.

In a preferred embodiment of the present invention, one may select analogs or derivatives of TG-25 having the structural attributes based on a pharmacophore of the TG-25 molecule having the general formula of the structure below:

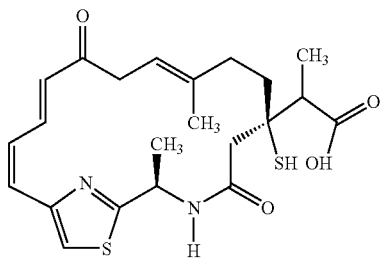

The TG-25 pharmacophore can be used to rationally choose or design analogs or derivatives with the same attributes as the lead compound that may be more effective as therapeutic agents.

Thus, one may design drugs which have improved biological activity, such as for example, inhibition of cell growth, inhibit DNA synthesis, DNA cleavage, cell cycle arrest, growth inhibition, or induction of apoptosis, relative to starting TG-25 compound. By virtue of the chemical isolation procedures and descriptions herein, sufficient amounts of the TG-25 compounds of the invention can be produced to perform crystallographic studies. In addition, knowledge of the chemical characteristics of these compounds permits computer employed predictions of structure-function relationships. Computer models of various chemical structures are also available in the literature or computer databases. Such databases may be used by one of ordinary skill in the art to identify TG-25 analogs.

Figure 2:
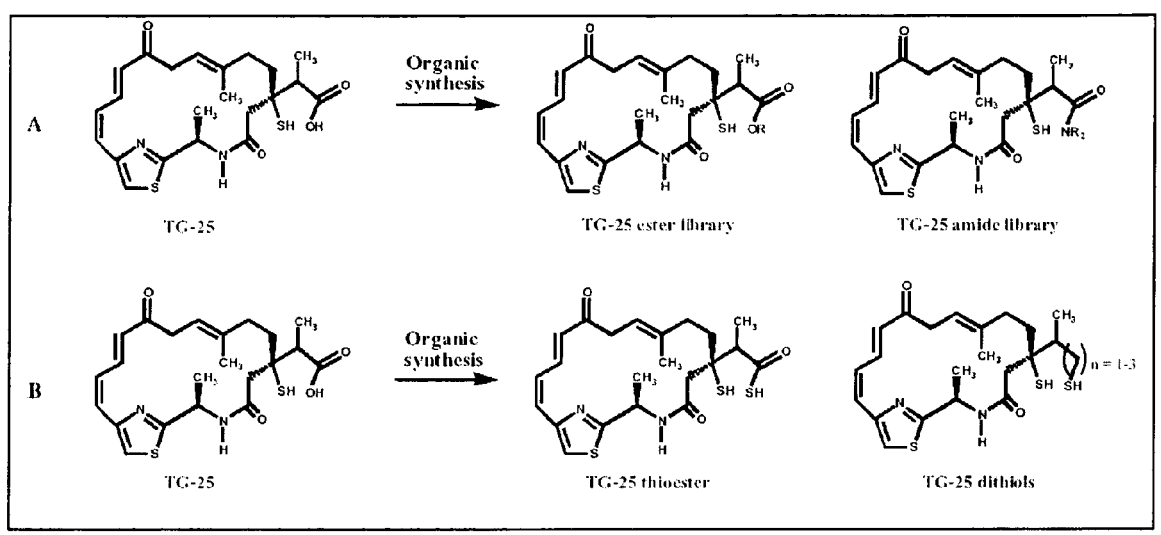
FIG. 2A and FIG. 2B show potiential TG-25 analogs.

In certain embodiments, the carboxyl group of TG-25 is used to perform variations and to determine the effectiveness of these variations on the production of an episulfonium ion which is activated under oxidative conditions. Some of these exemplary variations to the carboxyl group are illustrated in FIG. 2A. Various esters and amides of TG-25 are prepared according to standard methods. Further variations can be explored by altering R groups and determining the effect of the size, polarity, and hydrophility/hydrophobicity of the R-groups on the TG-25 on the activities against cultured prostate cells.

Further exemplary variations of TG-25 are shown in FIG. 2B. These variations are centered at the thiol group (FIG. 2B) such that they could be oxidatively activated by forming intramolecular disulfide bonds in contrast to TG-25 that forms the intermolecular disulfide intermediate. Both the TG-25 thioester and TG-25 dithiols can be prepared according to standard methods. These analogs will allow the probing of the TG-25 scaffolds' ability to form intramolecular disulfide linkage under oxidative activation and the resultant ability of TG-25 disulfides to generate the critical episulfornium ion for alkylative DNA damage.

Yet further, it is envisioned that other variations of the synthetic methodologies could easily allow be used to create additional structural diversity at the macrolactam ring of TG-25 by manipulation of genes governing TG-25 biosynthesis (Cheng et al., 2002; Du et al., 2001; Shen et al., 2001; Cheng et al., 2003; and Tang et al., 2004).

The term "drug" is intended to refer to a chemical entity, whether in the solid, liquid, or gaseous phase which is capable of providing a desired therapeutic effect when administered to a subject. The term "drug" should be read to include synthetic compounds, natural products and macromolecular entities such as polypeptides, polynucleotides, or lipids and also small entities such as ligands, hormones or elemental compounds. The term "drug" is meant to refer to that compound whether it is in a crude mixture or purified and isolated.

Methods of Treatment

In a particular aspect, the present invention provides methods for the treatment of cancer, wherein the cancer is characterized by cells having an oxidative cellular environment. The present invention relates to a TG-25 or an analog thereof that shows unexpected, potent anti-cancer activity in vitro. This compound cleaves DNA thus inhibiting cell growth, and is therefore useful in the treatment of diseases of uncontrolled proliferation, such as cancer, more specifically prostate cancer. Thus, the present invention provides TG-25 or an analog thereof as a therapeutic agent for treating a cancer in a subject.

Treatment methods will involve treating an individual with an effective amount of a composition containing TG-25 compound and/or analogs thereof. An effective amount is described, generally, as that amount sufficient to detectably and repeatedly to ameliorate, reduce, minimize or limit the extent of a disease or its symptoms. More specifically, it is envisioned that the treatment with the TG-25 compound or analogs thereof will kill cells, inhibit cell growth, cleave DNA, inhibit DNA synthesis, inhibit metastasis, decrease tumor size and otherwise reverse or reduce the malignant phenotype of tumor cells.

In certain embodiments, the TG-25 compound and/or analogs thereof are administered to a cell. Cells that are encompassed by the present invention include, but are not limited to prostate cells. More specifically, the prostate cell is a cancer cell, a non-cancerous cell or a benign hyperplastic cell. A cancer cell may include, cells that are drug-resistant, primary cancer cells and/or metastatic cancer cells.

Other cells as contemplated in the present invention may be a cancer cell such as, but not limited to, a breast cancer cell, lung cancer cell, head and neck cancer cell, bladder cancer cell, bone cancer cell, bone marrow cancer cell, brain cancer cell, colon cancer cell, esophageal cancer cell, gastrointestinal cancer cell, gum cancer cell, kidney cancer cell, liver cancer cell, nasopharynx cancer cell, ovarian cancer cell, prostate cancer cell, skin cancer cell, stomach cancer cell, testis cancer cell, tongue cancer cell, or uterine cancer cell.

An effective amount of TG-25 that may be administered to a cell includes a dose of about –0.1 μM to about 100 μM.

More specifically, doses of TG-25 to be administered are from about −0.1 µM to about 1 µM; about 1 µM to about 5 µM; about 5 µM to about 10 µM; about 10 µM to about 15 µM; about 15 µM to about 20 µM; about 20 µM to about 30 µM; about 30 µM to about 40 µM; about 40 µM to about 50 µM; about 50 µM to about 60 µM; about 60 µM to about 70 µM; about 70 µM to about 80 µM; about 80 µM to about 90 µM; and about 90 µM to about 100 µM. Of course, all of these amounts are exemplary, and any amount in-between these points is also expected to be of use in the invention.

In further aspects, an effective amount of a TG-25 compound or analog thereof may be administered to a subject suffering from prostate cancer, more specifically, recurrent prostate cancer. The effectiveness of the TG-25 therapy according to the present invention can be determined in the treatment of prostate cancer by diagnostic methods that are known and used in the art, for example, but not limited to, analysis of prostate specific antigen (PSA), a prostate biopsy, a rectal exam, or analysis of PSA and rectal exam.

Other embodiments include methods for inhibiting development of prostate cancer in a subject at risk, inhibiting prostate cancer metastasis in a subject with primary prostate cancer, and/or inhibiting prostate cancer progression in subjects having Stage 1 or Stage 2 prostate cancer.

Also within the scope of the invention is a method of treating benign prostate hyperplasia in a human subject afflicted with benign prostate hyperplasia comprising administering the TG-25 compound and/or analogs thereof to the subject in an amount and duration sufficient to result in alkylative DNA cleavage, inhibit DNA synthesis, cell killing, etc. The levels of prostate specific antigen (PSA) produced by the hyperplastic cells could also be stabilized or reduced upon treatment with TG-25 or analogs thereof.

The effective amount or "therapeutically effective amounts" of the TG-25 compound or analogs thereof to be used are those amounts effective to produce beneficial results, particularly with respect to cancer treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as TG-25 or analogs thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

A therapeutically effective amount of TG-25 or analogs thereof as a treatment varies depending upon the host treated and the particular mode of administration. In one embodiment of the invention the dose range of the TG-25 or analogs thereof will be about 0.5 mg/kg body weight to about 500 mg/kg body weight. The term "body weight" is applicable when an animal is being treated. When isolated cells are being treated, "body weight" as used herein should read to mean "total cell weight". The term "total weight may be used to apply to both isolated cell and animal treatment. All concentrations and treatment levels are expressed as "body weight" or simply "kg" in this application are also considered to cover the analogous "total cell weight" and "total weight" concentrations. However, those of skill will recognize the utility of a variety of dosage range, for example, 1 mg/kg body weight to 450 mg/kg body weight, 2 mg/kg body weight to 400 mg/kg body weighty, 3 mg/kg body weight to 350 mg/kg body weighty, 4 mg/kg body weight to 300 mg/kg body weight, 5 mg/kg body weight to 250 mg/kg body weighty, 6 mg/kg body weight to 200 mg/kg body weight, 7 mg/kg body weight to 150 mg/kg body weighty, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for TG-25 or analogs thereof.

Administration of the therapeutic TG-25 composition of the present invention to a patient or subject will follow general protocols for the administration of chemotherapeutics, taking into account the toxicity, if any, of TG-25. It is expected that the treatment cycles would be repeated as necessary. It also is contemplated that various standard therapies, as well as surgical intervention, may be applied in combination with the described therapy.

The treatments may include various "unit doses." Unit dose is defined as containing a predetermined-quantity of the therapeutic composition (TG-25 or its analogs thereof) calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

According to the present invention, one may treat the cancer by directly injection a tumor with the TG-25 or analog composition. Alternatively, the tumor may be infused or perfused with the composition using any suitable delivery vehicle. Local or regional administration, with respect to the tumor, also is contemplated. More preferably, systemic administration or oral administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs. For tumors of >4 cm, the volume to be administered will be about 4–10 ml (preferably 10 ml), while for tumors of <4 cm, a volume of about 1–3 ml will be used (preferably 3 ml). Multiple injections delivered as single dose comprise about 0.1 to about 0.5 ml volumes.

In certain embodiments, the tumor being treated may not, at least initially, be resectable. Treatments with therapeutic TG-25 compositions may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

Combined Cancer Therapy with TG-25 and/or Other Anticancer Agents

In the context of the present invention, it is contemplated that the TG-25 or analogs thereof may be used in combination with an additional therapeutic agent to more effectively treat prostate cancer. Anticancer agents may include but are not limited to, radiotherapy, chemotherapy, gene therapy, hormonal therapy or immunotherapy that targets cancer/tumor cells.

When an additional therapeutic agent is administered, as long as the dose of the additional therapeutic agent does not exceed previously quoted toxicity levels, the effective amounts of the additional therapeutic agent may simply be defined as that amount effective to inhibit and/or reduce the cancer growth when administered to an animal in combination with the TG-25 or analogs thereof. This may be easily determined by monitoring the animal or patient and measuring those physical and biochemical parameters of health and disease that are indicative of the success of a given treatment. Such methods are routine in animal testing and clinical practice.

To kill cells, induce cell-cycle arrest, inhibit cell growth, inhibit metastasis, inhibit angiogenesis or otherwise reverse or reduce the malignant phenotype of cancer cells, using the methods and compositions of the present invention, one would generally contact a cell with TG-25 or analogs thereof in combination with an additional therapeutic agent. These compositions would be provided in a combined amount effective to inhibit cell growth and/or induce apoptosis in the cell. This process may involve contacting the cells with TG-25 or analogs thereof in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes the TG-25 or derivatives thereof and the other includes the additional agent.

Alternatively, treatment with TG-25 or analogs thereof may precede or follow the additional agent treatment by intervals ranging from minutes to weeks. In embodiments where the additional agent is applied separately to the cell, one would generally ensure that a significant period of time did not expire between the time of each delivery, such that the agent would still be able to exert an advantageously combined effect on the cell. In such instances, it is contemplated that one would contact the cell with both modalities within about 12–24 hr of each other and, more preferably, within about 6–12 hr of each other, with a delay time of only about 12 hr being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either TG-25 or analogs thereof in combination with an additional therapeutic agent such as anticancer agent will be desired. Various combinations may be employed, where TG-25 or analogs thereof is "A" and the additional therapeutic agent is "B", as exemplified below:

A/B/A B/A/B B/B/A A/A/B B/A/A A/B/B B/B/B/A
  B/B/A/B
A/A/B/B A/B/A/B A/B/B/A B/B/A/A B/A/B/A B/A/A/B
  B/B/B/A
A/A/A/B B/A/A/A A/B/A/A A/A/B/A A/B/B/B B/A/B/B
  B/B/A/B

Chemotherapeutic Agents

In some embodiments of the present invention chemotherapy may be administered, as is typical, in regular cycles. A cycle may involve one dose, after which several days or weeks without treatment ensues for normal tissues to recover from the drug's side effects. Doses may be given several days in a row, or every other day for several days, followed by a period of rest. If more than one drug is used, the treatment plan will specify how often and exactly when each drug should be given. The number of cycles a person receives may be determined before treatment starts (based on the type and stage of cancer) or may be flexible, in order to take into account how quickly the tumor is shrinking. Certain serious side effects may also require doctors to adjust chemotherapy plans to allow the patient time to recover.

Chemotherapeutic agents that may be used in combination with TG-25 or an analog thereof in the treatment of cancer, include, but are not limited to cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, gemcitabien, navelbine, farnesyl-protein tansferase inhibitors, transplatinum, 5-fluorouracil and methotrexate, or any analog or derivative variant of the foregoing.

Radiotherapeutic Agents

Radiotherapeutic agents may also be use in combination with the compounds of the present invention in treating a cancer. Such factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Immunotherapeutic Agents

Immunotherapeutics may also be employed in the present invention in combination with TG-25 or analogs thereof in treating cancer. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the G1. The activity of this enzyme may be to phosphorylate Rb at late G1. The activity of CDK4 is controlled by an activating subunit, D-type cyclin, and by an inhibitory subunit, the p16INK4 has been biochemically characterized as a protein that specifically binds to and inhibits CDK4, and thus may regulate Rb phosphorylation (Serrano et al., 1993; Serrano et al., 1995). Since the p16INK4 protein is a CDK4 inhibitor (Serrano, 1993), deletion of this gene may increase the activity of CDK4, resulting in hyperphosphorylation of the Rb protein. p16 also is known to regulate the function of CDK6.

p16INK4 belongs to a newly described class of CDK-inhibitory proteins that also includes p16B, p19, p21WAF1, and p27KIP1. The p16INK4 gene maps to 9p21, a chromosome region frequently deleted in many tumor types. Homozygous deletions and mutations of the p16INK4 gene are frequent in human tumor cell lines. This evidence suggests that the p16INK4 gene is a tumor suppressor gene. This interpretation has been challenged, however, by the observation that the frequency of the p16INK4 gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type p16INK4 function by transfection with a plasmid expression vector reduced colony formation by some human cancer cell lines (Okamoto, 1994; Arap, 1995).

Other genes that may be employed according to the present invention include Rb, mda-7, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

Regulators of Programmed Cell Death

Apoptosis, or programmed cell death, is an essential process in cancer therapy (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Members of the Bcl-2 that function to promote cell death such as, Bax, Bak, Bik, Bim, Bid, Bad and Harakiri, are contemplated for use in combination with TG-25 or an analog thereof in treating cancer.

Surgery

It is further contemplated that a surgical procedure may be employed in the present invention. Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks every 1, 2, 3, 4, 5, 6, 7, 8, 9, 10, 11, or 12 months. These treatments may be of varying dosages as well.

Hormonal Therapy

Hormonal therapy may also be used in conjunction with the TG-25 or analog thereof as in the present invention, or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

Other agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increased intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Formulations and Routes for Administration of TG-25 or Analogs Thereof

Where clinical applications are contemplated, it will be necessary to prepare pharmaceutical compositions of TG-25 or analogs thereof, or any additional therapeutic agent disclosed herein in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention in an effective amount may be dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The composition(s) of the present invention may be delivered orally, nasally, intramuscularly, intraperitoneally, or intratumorally. In some embodiments, local or regional delivery of TG-25 or analogs thereof, alone or in combination with an additional therapeutic agent, to a patient with cancer or pre-cancer conditions will be a very efficient method of delivery to counteract the clinical disease. Similarly, chemo- or radiotherapy may be directed to a particular, affected region of the subject's body. Regional chemotherapy typically involves targeting anticancer agents to the region of the body where the cancer cells or tumor are located. Other examples of delivery of the compounds of the present invention that may be employed include intra-arterial, intracavity, intravesical, intrathecal, intrapleural, and intraperitoneal routes.

Intra-arterial administration is achieved using a catheter that is inserted into an artery to an organ or to an extremity. Typically, a pump is attached to the catheter. Intracavity administration describes when chemotherapeutic drugs are introduced directly into a body cavity such as intravesical (into the bladder), peritoneal (abdominal) cavity, or pleural (chest) cavity. Agents can be given directly via catheter. Intravesical chemotherapy involves a urinary catheter to provide drugs to the bladder, and is thus useful for the treatment of bladder cancer. Intrapleural administration is accomplished using large and small chest catheters, while a Tenkhoff catheter (a catheter specially designed for removing or adding large amounts of fluid from or into the peritoneum) or a catheter with an implanted port is used for intraperitoneal chemotherapy. Abdomen cancer may be treated this way. Because most drugs do not penetrate the blood/brain barrier, intrathecal chemotherapy is used to reach cancer cells in the central nervous system. To do this, drugs are administered directly into the cerebrospinal fluid. This method is useful to treat leukemia or cancers that have spread to the spinal cord or brain.

Alternatively, systemic delivery of the chemotherapeutic drugs may be appropriate in certain circumstances, for example, where extensive metastasis has occurred. Intravenous therapy can be implemented in a number of ways, such as by peripheral access or through a vascular access device (VAD). A VAD is a device that includes a catheter, which is placed into a large vein in the arm, chest, or neck. It can be used to administer several drugs simultaneously, for long-term treatment, for continuous infusion, and for drugs that are vesicants, which may produce serious injury to skin or muscle. Various types of vascular access devices are available.

The active compositions of the present invention may include classic pharmaceutical preparations. Administration of these compositions according to the present invention will be via any common route so long as the target tissue is available via that route. This includes but is not limited to, oral, nasal, or buccal routes. Alternatively, administration may be by orthotopic, intradermal, subcutaneous, intramuscular, intraperitoneal or intravenous injection. Such compositions would normally be administered as pharmaceutically acceptable compositions, described supra. The drugs and agents also may be administered parenterally or intraperitoneally. The term "parenteral" is generally used to refer to drugs given intravenously, intramuscularly, or subcutaneously.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The therapeutic compositions of the present invention may be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH, exact concentration of the various components, and the pharmaceutical composition are adjusted according to well known parameters. Suitable excipients for formulation with TG-25 or analogs thereof include croscarmellose sodium, hydroxypropyl methylcellulose, iron oxides synthetic), magnesium stearate, microcrystalline cellulose, polyethylene glycol 400, polysorbate 80, povidone, silicon dioxide, titanium dioxide, and water (purified).

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Microorganisms and Culture Conditions

The wild-type LNM producer $S.$ $atroolivaceus$ and the $\Delta lnmE$ mutant were fermented as follows. Five microliters of spore suspension were inoculated into a 250 ml baffled flask containing 50 ml of seed medium (glucose 1%, soluble starch 1%, beef extract 0.3% yeast extract 0.5%, Bacto-tryptone 0.5%, $CaCO_3$ 0.2%, and glass beads/liter, pH 7.2 before sterilization), and fermentation was carried out on a shaking incubator at 28° C. with 300 rpm for 2 days. Five milliliters of seed medium was transferred into a 250 ml baffled flasks containing 50 ml of production medium (soluble starch 4%, soybean meal 0.5%, corn steepliquor 0.5%, $KH_2PO_4$ 0.05%, $MgSO_4$ 0.025%, $ZnSO_4.7H_2O$ 0.004%, L-methionine 0.01%, vitamin B12 0.0004%, $CaCO_3$ 0.5%, Diaion HP-20 resin 5%, pH 7.0 before sterilization), and fermentation was carried out on a shaking incubator at 28° C. with 300 rpm for 4–6 days.

Example 2

Inactivation of lnmE in $Streptomyces$ $atroolivaceus$ S-140

A 4.2-kb EcoRI fragment from cosmid pBS3005, which contained the entire lnmC, lnmD, lnmE, lnmF and N-terminal of lnmG, was subcloned into pSP72 to yield pTGC23. Then, a 0.9-kb XhoI-NotI fragment containing the N-terminal of lnmE from pTGC23 was moved into the same sites of pGEM-11Zf(+) to yield pTGS36; a 0.76-kb XhoI-NotI fragment containing the C-terminal of lnmE from pTGC23 was moved into the same sites of pGEM-11Zf(+) to yield pTGS37; and a 1.3-kb BamHI fragment containing the C-terminal of lnmE and the entire lnmF from pTGC23 was subcloned into the same sites of pSET151 to yield pTGS38. Finally, a 0.9-kb EcoRI-NotI fragment containing the N-terminal of lnmE from pTGS36, a 1.5-kb NotI-BamHI fragment containing the aac(3)IV apramycin-resistant gene, and a 0.4-kb BamHI-XhoI fragment containing the C-terminal of lnmE from pTGS37 were ligated and cloned into EcoRI/XhoI sites of pTGS38 to yield to yield pTG25. This construct was introduced into $S.$ $atroolivaceus$ S-140 by conjugation and selected for apramycin resistance and thiostrepton-sensitive phenotype to isolate the desired double-crossover mutant strain TG25 ($\Delta lnmE$).

The genotype was confirmed by Southern analysis (FIG. 3) using the 0.9-kb EcoRI-HindIII fragment from pTGS36 (left arm) as a probe. When the genomic DNA was digested with NcoI, a distinctive band of the predicted size of 3.2-kb was detected in the wide type strain (lane 5). In the $\Delta lnmE$ mutant strains, this band was split into two fragments, and only the 1.0-kb fragment could be detected (lane 2, 3 and 4).

Example 3

Detection of Leinamycin and Its New Analogs

The LNM wild-type and $\Delta lnmE$ mutant strains were cultured in LNM production medium, and the harvested broth was acidified to pH 2.0 with 1N HCl. Diaion HP-20 resins were recovered by filtering through two layers of cheese gauze and dried over by lyophilization. Secondary metabolites were extracted twice from the resins with methanol and analyzed by high-performance liquid chromatography (HPLC). HPLC for detection of LNM or LNM analogs was performed on an analytical reversed phase column (C18, 4.6×250 mm, Waters) on a ProStar-210 HPLC system with a photodiode array detector at 320 nm (Varian). A linear gradient from 20 to 80% aqueous acetonitrile, pH 3.6 with AcOH, in 45 min at a flow rate of 0.8 ml/min was used as elution solvent.

Figure 4:
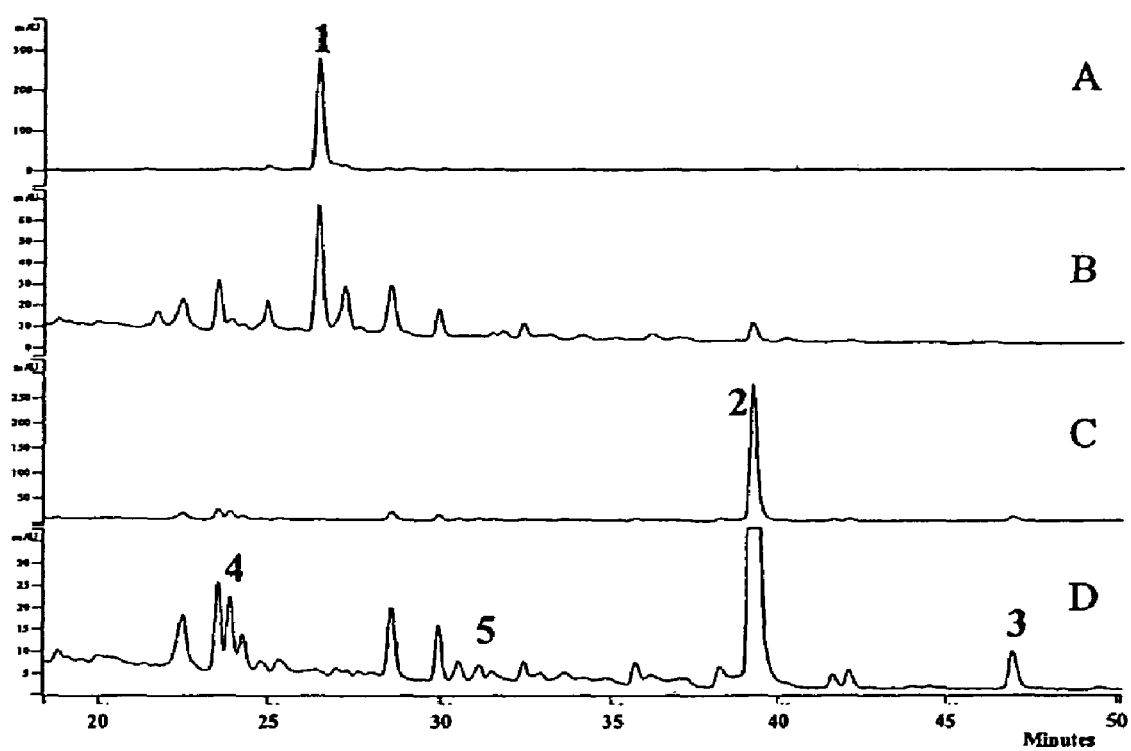
FIG. 4 shows HPLC profile of fermentation extract of the ΔlnmE mutant and wild type strains. A: LNM standard, B: wild-type, C: ΔlnmE mutant, and D: expansion of chromatogram C.

The production of LNM was abolished in all ΔlnmE mutants, whereas four new substances showing similar UV spectrum to LNM were produced in the mutants (FIG. 4).

Example 4

Isolation and Purification of the New LNM Analogs

In order to isolate new LNM analogs, fermentation of the ΔlnmE mutant strain was carried out under the same conditions as that of wild type strain with minor modification. The spore suspension (5 μl) of the mutant ΔlnmE was inoculated into 250 ml baffled flasks containing 50 ml of seed medium, and fermentation was carried out on a shaking incubator at 28° C. with 300 rpm for 2 days. Fifty milliliters of seed medium were transferred into 2-liters baffled flasks containing 400 ml production medium. Fermentation was carried out on a shaking incubator at 28° C. with 300 rpm for 5 days. The harvested fermentation broth was immediately acidified to pH 2.0 with 2N HCl and Diaion HP-20 resins were recovered by filtration through cheesecloth and then lyophilized to dryness. Crude LNM analogs were extracted from the HP-20 resins with methanol, and the methanol was concentrated under reduced pressure. The methanolic extract was partitioned between ethyl acetate and acidic water of pH 2.0. The ethyl acetate-soluble portion was dried over $Na_2SO_4$, filtered, and evaporated to give a dark brown residue. The residue was subjected to a column of Sephadex LH-20 eluting with chloroform/methanol (1/1, v/v) to give two fractions. Prior fraction was rechromatographed on Sephadex LH-20 column eluting with methanol to give a dimeric compound 3. Second fraction was chromatographed on a column of silica gel eluting with chloroform/methanol (15/1, v/v), followed by Sephadex LH-20 column chromatography eluting with methanol to give a mixture of 2, 4, and 5. Finally the mixture was purified by preparative thin-layer chromatography (TLC) developed with chloroform:methanol (15/1, v/v).

Example 5

Analytical Method

The structures of new LNM analogs were elucidated by NMR spectroscopy and mass spectrometry. All NMR spectra were obtained using a Varian UNITY Inova spectrometer (400 MHz for $^1H$ and 100 MHz for $^{13}C$) in $CD_3OD$ or a mixture of $CDCl_3$ and $CD_3OD$ (1/1,v/v) with TMS as an internal standard. Chemical shifts are given in ppm (δ) values. The electrospray ionization (ESI) mass spectra were acquired using an Agilent 1100 Series LC/MSD electrospray system in positive and negative modes. The high-resolution MALDI mass spectra were taken on an IonSpec Ultima Fourier Transform mass spectrometer in positive mode. The UV spectra were recorded on a Shimadzu UV-1601 UV-visible spectrophotometer. The $^1H$-NMR spectral data for 2, 3, 4, and 5 are listed in Table 1, and the $^{13}C$-NMR spectral data for 2 and 4 are listed in Table 2. These assignments are based on two-dimensional spectra including COSY, HMQC and HMBC spectra. Analytical $SiO_2$ TLC was performed with Kiesel gel $60F_{254}$ (Merck) without activation.

Example 6

Characterization of Unnatural Natural Principles from the ΔlnmE Mutant

While the ΔlnmE mutant completely abolished LNM production, it produced four new LNM derivatives. These compounds were isolated on a preparative scale with yields of 14.0 mg/L for the major component 2 and 0.4, 0.7, and 0.6 mg/L for minor components 3, 4, and 5, respectively. Component 2 was slowly converted into its symmetrical dimmer 3 and rearranged to 4 and 5 during isolation. The structures of these compounds were determined as shown in FIG. 5 by spectroscopic methods. The UV spectra of these compounds were similar to that of LNM showing an UV maximum at 320 nm. That implied that these compounds are structurally related to LNM. The molecular formula of 2 was determined to be $C_{22}H_{28}O_4N_2S_2$ by high-resolution MALDI mass measurement [found 449.159 $(M+H)^+$, calcd 449.157; found 471.141 $(M+Na)^+$, calcd 471.139] in combination with $^1H$ and $^{13}C$ NMR spectra. The comparison of the $^1H$ and $^{13}C$ NMR spectra of 2 with those of LNM revealed that LNM signals derived from C-9 to C-17 were conserved in 2. That was consistent with the UV spectrum, which suggested that 2 had the same chromophore as LNM. The difference between 2 and LNM was in the hydroxylated carbons and dithiolane moiety. Two hydrogenated carbons (C-8 and C-2') and one carbonyl carbon (C-1', $δ_C$ 205) in LNM were missing in 2, while two $sp^3$ methylene (C-8, $δ_H$: 3.46, 3.27,$δ_C$: 40.7) and one methine (C-2', $δ_H$: 2.96,$δ_C$: 47.6) peaks and one carbonyl carbon (C-1', $δ_C$ 176.5) peak were newly observed in 2. The structure was confirmed by two-dimensional NMR experiments including $^1H$-$^1H$ COSY and HMBC. The vicinal and allylic couplings in COSY spectrum revealed the five partial structures, which were connected by HMBC. Methylene protons at δ 3.46 and 3.27 (H-8) showed long-range correlations to a carbonyl carbon at δ201.8 (C-9) and to two $sp^2$ carbons at δ 139.5 (C-6) and 118.7 (C-7), revealing that hydroxyl group of C-8 in LNM was missed in 2. Another critical long-range couplings were observed between the methyl protons at δ1.28 (H-3') and the quaternary carbon at δ50.5 (C-3) and the carbonyl carbon at δ176.5 (C-1'). These correlations suggested that thioester group in LNM was displaced with carboxylic acid in 2. Thioester carbonyl carbon in LNM appeared near δ 205 but the corresponding signal for 2 was shifted to δ176.5. Other important long-range couplings substantiating this structure were observed between H-2/C-1, 3, 4, H-7, 8, 11/C-9, H-14/C-13, 15, H-17/C-15, H-18/C-5, 7, H-3'/C-3.

Figure 3:
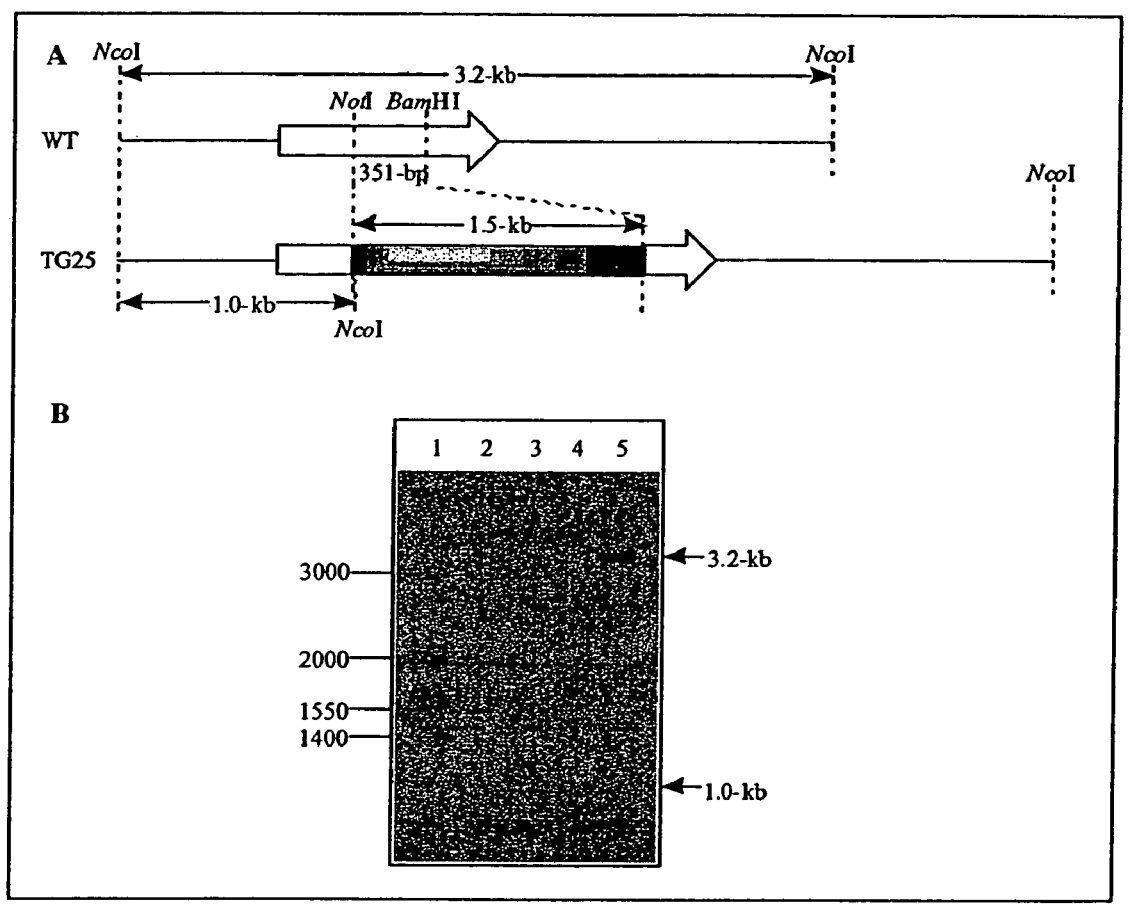
FIG. 3 illustrates Southern analysis of the ΔlnmE mutants (Lane 1, marker; lane 2, 3, 4, ΔlnmE mutants; lane 5, WT).

The structure of minor component 3 was determined by the comparison of NMR spectral data with those of 2 and mass analysis. The LC-ESI mass spectrometry in positive mode revealed a molecular ion peak of m/z 895 $(M+H)^+$, indicating that this compound has a dimeric structure. The $^1H$ NMR spectrum of 3 was almost identical to that of 2, and the partial structures assigned by the COSY spectrum were identical with those of 2, as shown in FIG. 3. These results implied that 3 was a symmetrical dimer of 2. The structure was supported by the molecular formula $C_{44}H_{54}O_8N_4S_4$ by high-resolution MALDI mass measurement in the positive mode [found 895.293 $(M+H)^+$, calcd 895.291; found 917.276 $(M+Na)^+$, calcd 917.273]. Dimerization of thiol compounds by reduction to give disulfide bond is a ubiquitous in natural products.

The $^1H$ and $^{13}C$ NMR spectra of 4, in combination with the LC-ESI mass spectra, which revealed molecular ion peaks of m/z 465 $(M+H)^+$ in the positive mode and m/z 463

(M–H)⁻ in the negative mode, indicated the molecular formula to be $C_{22}H_{28}O_5N_2S_2$. This was verified by high resolution MALDI mass spectrometry [found 465.156 (M+H)⁺, calcd 465.152; found 487.138 (M+Na)⁺, calcd 487.134]. The comparison of $^1H$, $^{13}C$, and DEPT spectra with those of 2 showed that proton and carbon chemical shifts ranging C-2 to C-7 were significantly different between both compounds, especially the absence of two olefin carbons and the presence of additional sp³ methine (H-7, $\delta_H$: 3.7&$\delta_C$: 46.6) and oxygenated quaternary carbon (C-6, $\delta_C$: 72.6). The $^1H$-$^1H$ COSY spectrum established same partial structures as those of 2 except for one partial structure (—CH—CH₂—) composing of C-7 and C-8. HMBC connected these partial structures. The critical HMBC correlations from methyl protons at δ1.43 (H-18) to three carbons at δ37.8 (C-5), 72.6 (C-6), and 46.6 (C-7) revealed that double bond of C-6 in 2 was hydrated in 4. In the process of elimination, C-7 should be connected to C-3 by the bridge of sulfur ion to give thiacyclohexane moiety. 4 was a rearranged product of 2. LNM also rearranges to similar structure to 4 and this rearrangement process is known to be responsible for biological activity of LNM.

The $^1H$ NMR spectrum of 5 was identical as that of 4, except the presence of an additional methoxyl group. The LC-ESI mass measurement in positive mode revealed molecular ion peaks of m/z 479.2 (M+H)⁺ and m/z 501.2 (M+Na)⁺, which was 14 mass (CH₂) higher than that of 4. These spectral data suggested that the structure of 5 should be methoxy-4. 5 has two hydroxyl groups to be methylated at C-1 and C-6. The structure of 5 was assigned by high-field shift of methoxymethyl protons (δ 3.02) as 6-methoxy-4, which was also supported by a HMBC cross-peak from methyl protons at δ 3.02 to the carbon corresponding to C-6 of 4. The $^1H$ NMR spectral data of 2, 3, 4, and 5 and $^{13}C$ NMR spectral data of 2 and 4 are summarized in Tables 1 and 2, respectively.

The regiochemistry of C-10 and C-12 of all compounds was determined as trans and cis-geometry, respectively, by coupling constants of 16–17 Hz and 11.2 Hz, and olefinic proton of C-6 of 1 as trans by γ-effect, which caused the up-field shift of C-18. Other stereochemistry except for olefinic protons was deduced from that of LNM.

TABLE 2

$^{13}C$ NMR spectral data of compounds 2 and 4 in CD₃OD and CDCl₃ (1:1, v/v)

| No. | 2 | 4 |
|---|---|---|
| 1 | 171.1 | 170.4 |
| 2 | 45.4 | 38.9 |
| 3 | 50.5 | 47.5 |
| 4 | 37.6 | 30.3 |
| 5 | 34.5 | 37.8 |
| 6 | 139.5 | 72.6 |
| 7 | 118.7 | 46.6 |
| 8 | 40.7 | 40.5 |
| 9 | 201.8 | 202.4 |
| 10 | 131.3 | 133.2 |
| 11 | 144.7 | 142.2 |
| 12 | 128.0 | 128.6 |
| 13 | 129.0 | 128.7 |
| 13a | 154.0 | 152.8 |
| 14 | 121.7 | 121.7 |
| 15 | 169.6 | 172.5 |
| 16 | 48.0 | 48.4 |
| 17 | 21.4 | 21.7 |
| 18 | 15.7 | 18.1 |
| 1' | 176.5 | 176.9 |
| 2' | 47.6 | 44.5 |
| 3' | 13.2 | 12.0 |

Example 7

Oxidation Reaction

Three additional minor metabolites were also characterized from the ΔlnmE strain, and their structures were elucidated by the combination of MS, $^1H$- and $^{13}C$—NMR, and various 2D NMR spectroscopic methods as discussed above (compound 1, 2, 4, and 5 as shown in FIG. 6) Although these compounds were isolated in minor quantities and were apparently derived from TG-25 during the isolation, their structures were critical in helping to define the oxidative activation of TG-25 undergo rearrangement via an episulfornium ion intermediate (FIG. 6). It was clear by comparing the structure of TG-25 with those of 1 and 2 that an oxidation

TABLE 1

$^1H$ NMR spectral data of compounds 2, 3, 4, and 5 in CD₃OD and CDCl₃ (1:1, v/v)

Figure 6:
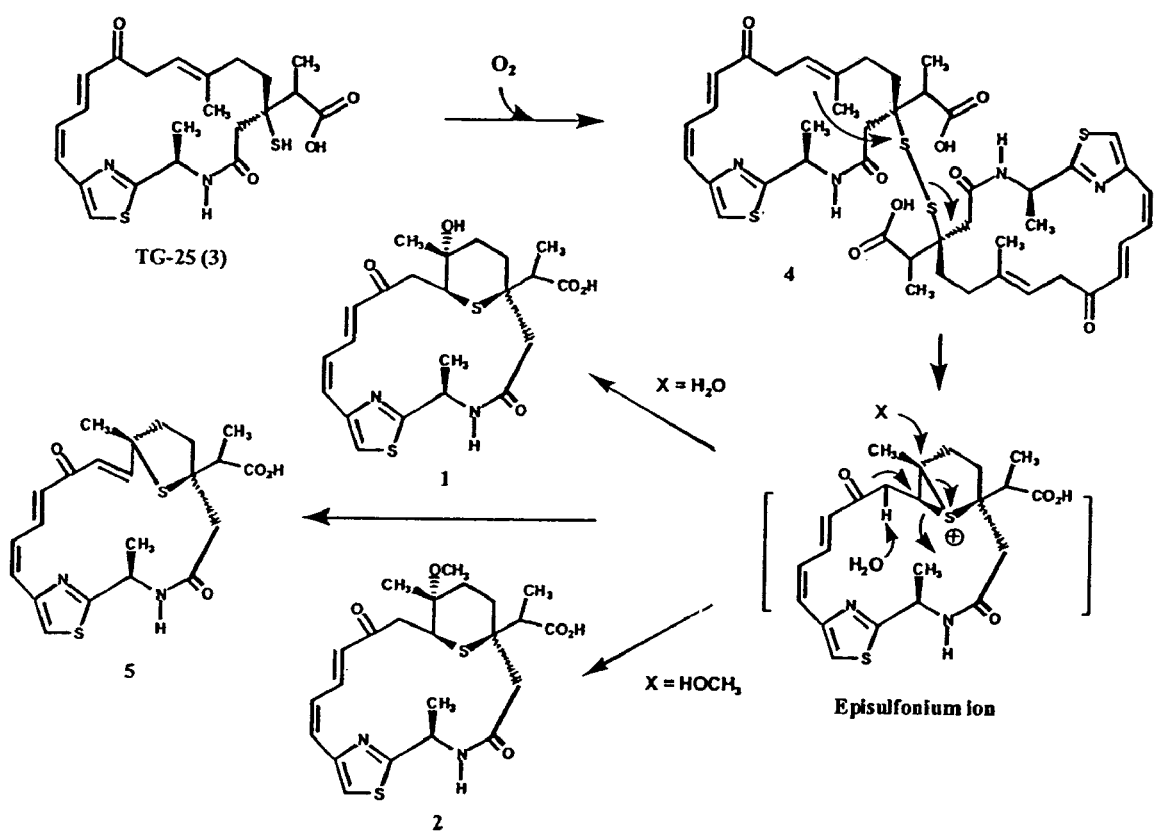
FIG. 6 shows the production of TG-25 produced by the genetically engineered *S. atroolovaceus* ΔlnmE mutant strain and its oxidized dimmer (4) and further rearrangement products 1 and 5 (in aqueous solution) or 2 in acidic methanol.

| No. | 2 | 3 | 4 | 5 |
|---|---|---|---|---|
| 2 | 2.77(1H, d, J=14.0)ᵃ | 2.33(1H, d, J=13.6) | 2.46(1H, d, J=14.6) | 2.42(1H, d, J=15.2) |
|  | 2.93(1H, d, J=14.0) | 3.05(1H, d, J=13.6) | 3.17(1H, d, J=14.6) | 3.19(1H, d, J=15.2) |
| 4 | 2.33(1H, m), 2.05(1H, m) | 2.34(1H, m), 2.13(1H, m) | 2.66(1H, m), 1.66(1H, m) | 2.60(1H, m), 1.60(1H, m) |
| 5 | 2.09(1H, m), 1.33(1H, m) | 2.13(1H, m), 1.33(1H, m) | 1.77(1H, m), 1.66(1H, m) | 1.86(1H, m), 1.60(1H, m) |
| 7 | 5.81(1H, dd, J=9.8, 6.2) | 5.96(1H, dd, J=9.8, 6.8) | 3.76(1H, dd, J=12.8, 3.6) | 3.86(1H, dd, J=12.4, 3.6) |
| 8 | 3.46(1H, dd, J=13.0, 6.2) | 3.57(1H, dd, J=13.2, 6.8) | 2.97(1H, dd, J=12.8, 3.6) | 2.88(1H, dd, J=12.4, 3.6) |
|  | 3.27(1H, dd, J=13.0, 9.8) | 3.28(1H, br t, J=11.8) | 2.36(1H, t, J=12.8) | 2.15(1H, t, J=12.4) |
| 10 | 5.99(1H, d, J=16.4) | 6.03(1H, d, J=16.2) | 6.11(1H, d, J=16.2) | 6.01(1H, d, J=16.0) |
| 11 | 9.04(1H, dd, J=16.4, 11.2) | 9.28(1H, dd, J=16.2, 11.2) | 8.64(1H, dd, J=16.2, 11.2) | 8.69(1H, dd, J=16.0, 11.2) |
| 12 | 6.36(1H, t, J=11.2) | 6.42(1H, t, J=11.2) | 6.35(1H, t, J=11.2) | 6.32(1H, t, J=11.2) |
| 13 | 6.67(1H, d, J=11.2) | 6.72(1H, d, J=11.2) | 6.67(1H, d, J=11.2) | 6.67(1H, d, J=11.2) |
| 14 | 7.43(1H, S) | 7.62(1H, S) | 7.47(1H, S) | 7.59(1H, S) |
| 16 | 5.23(1H, q, J=6.8) | 5.27(1H, q, J=6.8) | 5.32(1H, q, J=6.6) | 5.24(1H, q, J=6.4) |
| 17 | 1.64(3H, d, J=6.8) | 1.67(3H, d, J=6.8) | 1.72(3H, d, J=6.6) | 1.67(3H, d, J=6.4) |
| 18 | 1.70(3H, s) | 1.76(3H, s) | 1.43(3H, s) | 1.36(3H, s) |
| 2' | 2.96(1H, q, J=6.8) | 3.08(1H, q, J=6.8) | 3.67(1H, q, J=7.2) | 3.68(1H, q, J=7.4) |
| 3' | 1.28(3H, d, J=6.8) | 1.29(3H, d, J=6.8) | 1.26(3H, d, J=7.2) | 1.21(3H, d, J=7.4) |
| OCH₃ |  |  |  | 3.02(3H, s) |

ᵃProton resonance integral, multiplicity, and coupling constants (J=Hz)

step was required for their conversion. Isolation of compound 4 shed light into how this oxidative rearrangement from TG-25 to 1 or 2 actually happens. Thus, as depicted in FIG. 6 TG-25 apparently was first oxidized by $O_2$ to form the dimmer 4, activating the sulfhydryl group into a disulfide. Nucleophilic attack of the disulfide by the double bond could then be envisaged to form an episulfonium ion intermediate, in a mechanistic analogy to LNM, that subsequently could be trapped by $H_2O$ (leading the formation of 1) or methanol (leading to the formation of 2). This hypothesis was confirmed by re-producing the chemistry in vitro with purified TG-25. Indeed, TG-25, upon exposure to $O_2$, rapidly converted to 1 or 2 in aqueous or methanol solution, respectively, and small amount of 5 was also isolated in the in vitro reaction, which presumably resulted from direct rearrangement of the episulfonium ion intermediate as shown in FIG. 6, further supporting the proposed mechanism.

Strikingly, TG-25 genereateed a similar episulfornium ion intermediate, as evidenced by the isolation of 1, 2 or 5 (FIG. 6) as LNM. What is most remarkably is that, in contrast to LNM, the episulfonium ion formation from which must be under reductive environment requiring free RSH (FIG. 1A), TG-25 generates the episulfonium ion intermediate under an oxidative environment, requiring $O_2$ (FIG. 1B). Therefore while LNM and TG-25 both exploit a similar episulfonium ion to exert cytotoxicity by alkylative DNA cleavage, the mechanisms for episulfornium ion formation from LNM and TG-25 are distinct: reductive activation for LNM and oxidative activation for TG-25.

Example 8

In Vitro Inhibition of Prostate Cancer Cells

Figure 7:
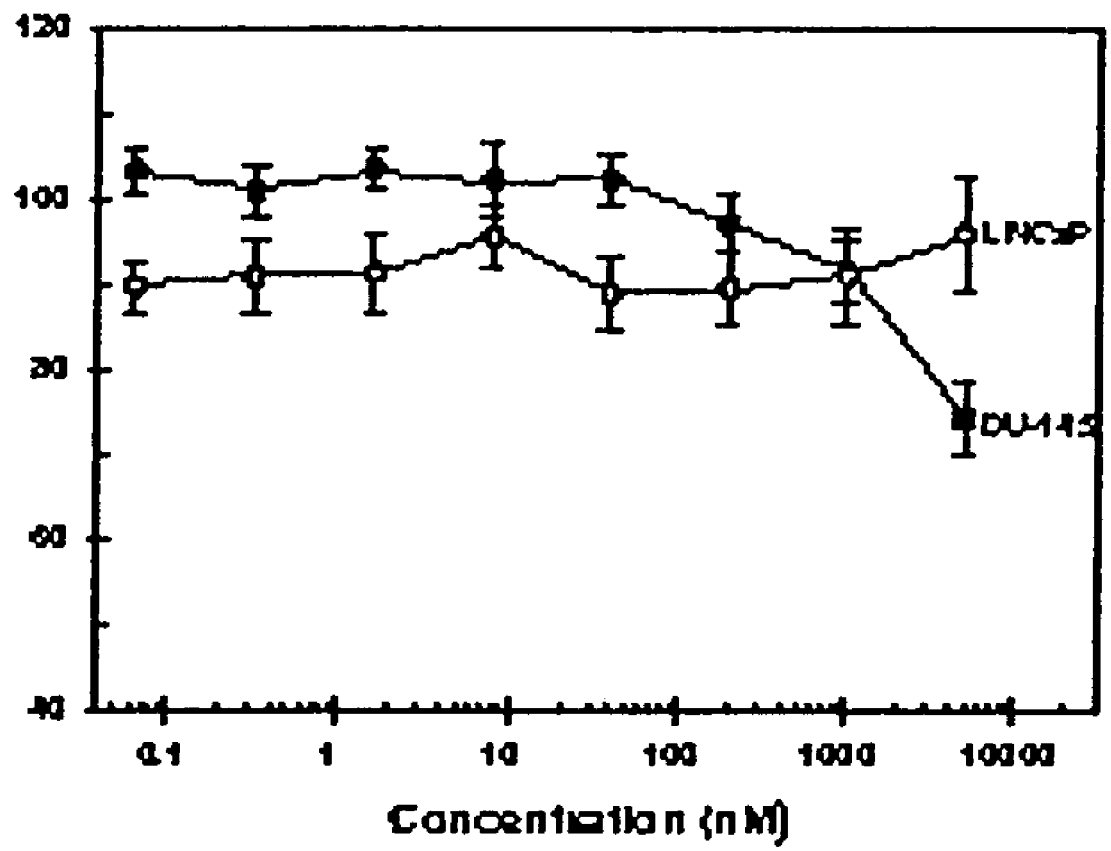
FIG. 7 shows the effect of leinamycin on the growth of DU-145 and LNCaP cells by DNA assay.

Using DCFH oxidation assay, it has previously been demonstrated that the oxidative stress differs between prostate cancer cell lines. LNCaP cells exhibit relatively more oxidative stress than do DU-145 cells. The growth inhibitory effects of LNM against LNCaP and DU-145 cell lines grown in 5% FBS were determined by measuring DNA fluorescence 72 h after drug treatment. LNM exhibited its cytotoxicity in the presence of cellular thiols such as glutathione found in many bacterial and tumor cells. Growth inhibitory effects of LNM against LNCaP and DU-145 cells were expressed as percent of control untreated cells are shown in FIG. 7. DU-145 cells that have relatively less reactive oxygen species (ROS) level and more glutathione level than have the LNCaP cells are slightly more sensitive to LNM than are the LNCaP cells.

Example 9

Growth Inhibitory Effects of LNM and TG-25

Figure 8:
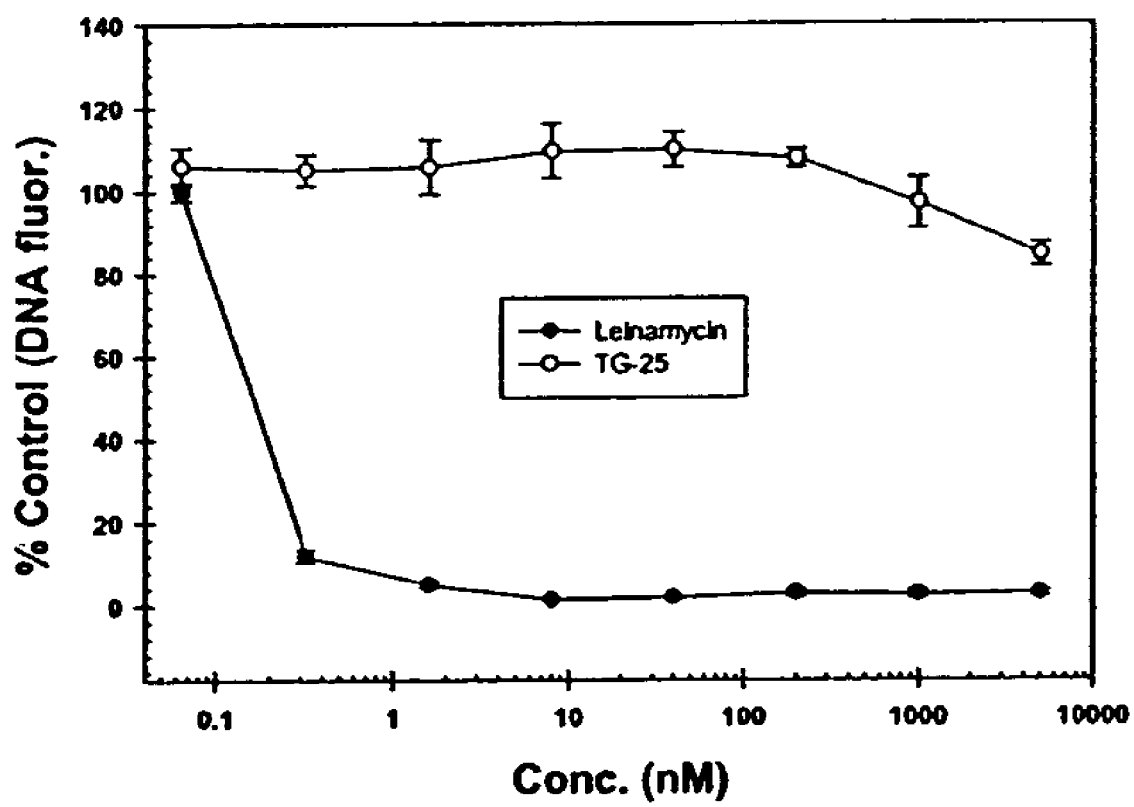
FIG. 8 shows the effect of leinamycin analogs on the growth of immortalized normal prostatic epithelial cells (E6) by DNA assay.

The growth inhibitory effects of LNM and TG-25 against immortalized normal prostatic epithelial cells are shown in FIG. 8. LNM was strongly growth inhibitory ($IC_{50}$<200 pM) against these cells, while TG-25 shows little growth inhibitory effect even at μM concentration. Also, LNM exhibited stronger growth inhibitory effect against these cell line than it did against the prostate cancer cell lines (FIG. 7) that were under greater oxidative stress.

Figure 9:
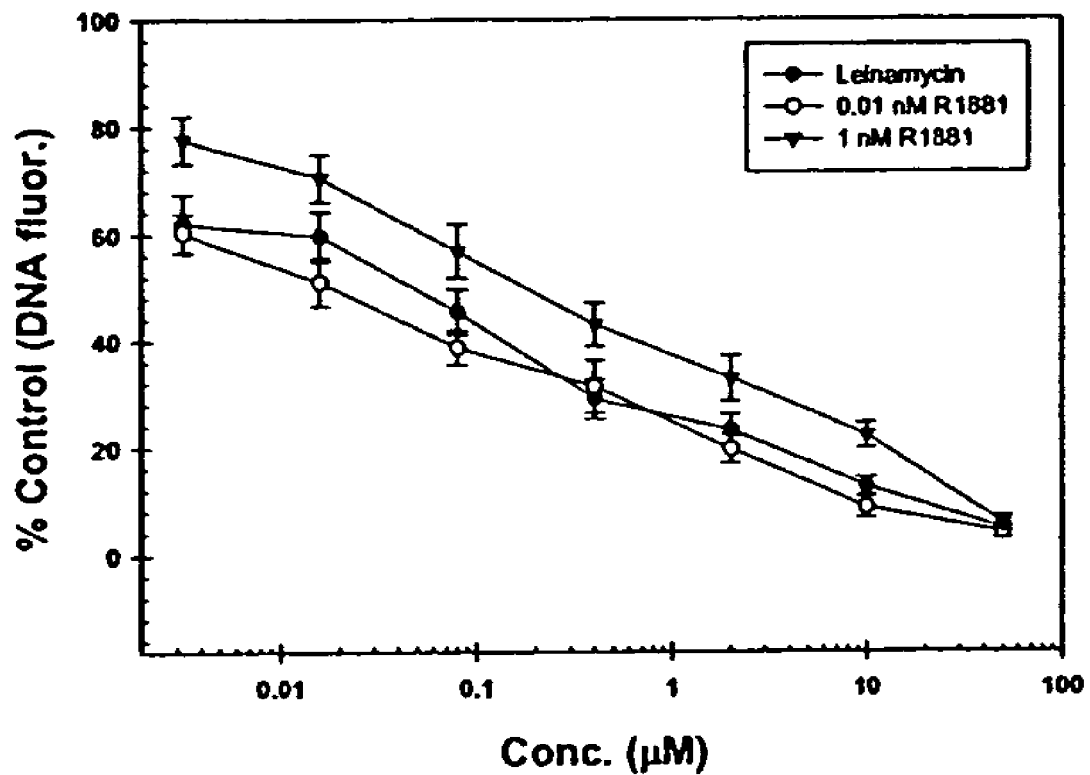
FIG. 9 shows the effect of leinamycin on the growth of LNCaP cells pretreated with R1881 by DNA assay.
Figure 10:
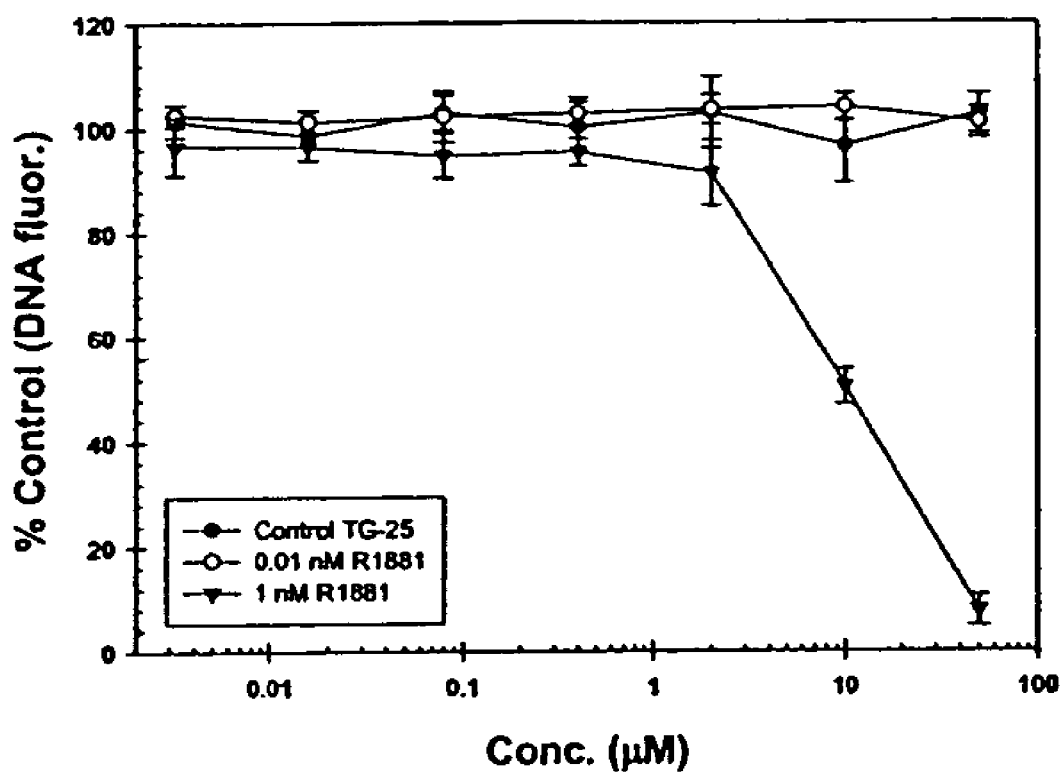
FIG. 10 shows the effect of TG-25 on the growth of LNCaP cells pretreated with R1881 by DNA assay.

To test whether TG-25 was activated under oxidative stress, LNCaP cells were grown in androgen-depleted medium in the presence of 0.01 nM and 1 nM androgen analog R1881 for 96 h. It has been established that under these conditions, 0.01 nM R1881 reduces the cellular ROS and 1 nM R1881 increases cellular ROS level as determined by a DCFH oxidation assay. This concentration was also close to the range of concentration of the active androgen dihydrotestosterone found in normal human male and patients treated with androgen ablation therapy. The growth inhibitory effect of LNM and TG-25 against LNCaP cells either untreated or pretreated with R1881 as shown in FIG. 9 and FIG. 10, respectively. Under these treatment conditions, 0.01 nM R1881 stimulated growth by about 30% and 1 nM R1881 inhibited cell growth to about 40% of the control untreated cells. The data shown in FIG. 9 and FIG. 10 are normalized for the growth stimulatory or inhibitory effects of R1881 alone. The growth inhibitory effect of LNM was more pronounced in LNCaP cells growing in androgen depleted medium (FIG. 9) than those growing in 5% FBS (FIG. 7). The growth inhibition by LNM was not appreciably affected by R1881 pretreatment (FIG. 9). While TG-25 had no effect against control untreated cells and cells pretreated with 0.01 nM R1881, it markedly inhibited the growth of R1881 pretreated cells (FIG. 10). These data indicated an activation of TG-25 under high oxidative stress conditions.

Example 10

Growth Inhibitory Effects of LNM and TG-25 Pretreated with Vitamin E

Figure 11:
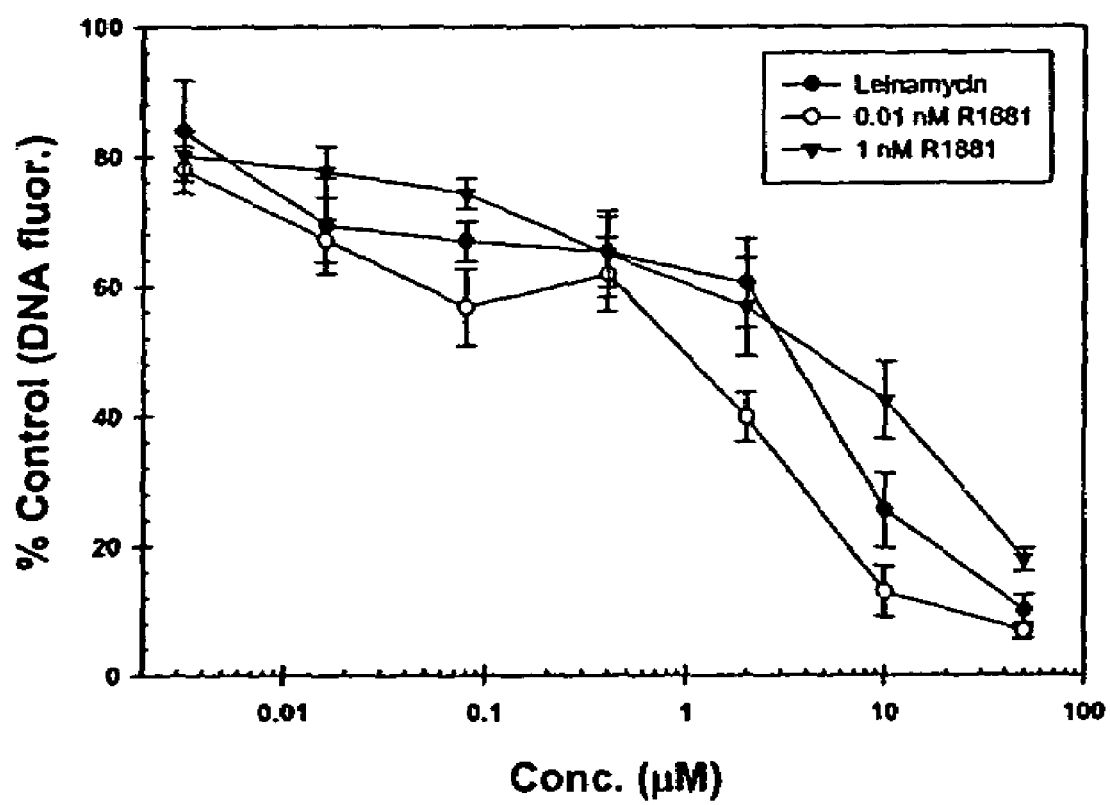
FIG. 11 shows the effect of leinamycin on the growth of LNCaP cells pretreated with vitamin E succinate+R1881 by DNA assay.
Figure 12:
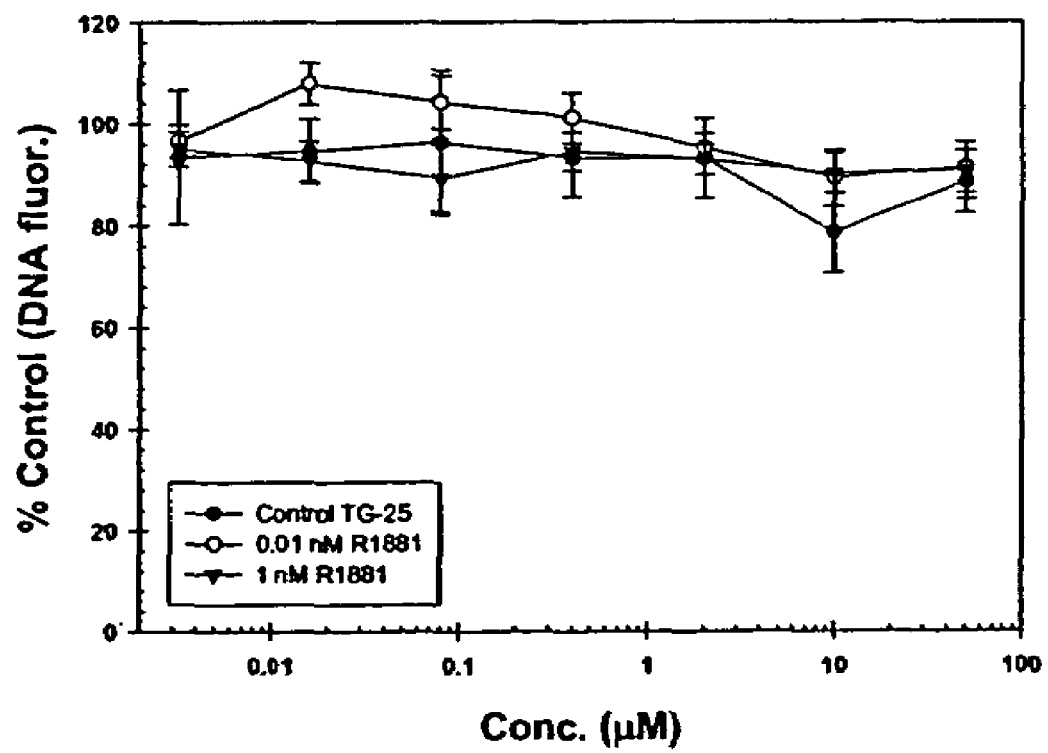
FIG. 12 shows the effect of TG-25 on the growth of LNCaP cells pretreated with vitamin E+R1881 by DNA assay.

It has been previously demonstrated that the increase in the ROS level by 1 nM R1881 pretreatment of LNCaP cells can be inhibited by co-treating cells with an antioxidant α-tocopherol (vitamin E) succinate. The effect of LNM and TG-25 against LNCaP cells pretreated with both R1881 and α-tocopherol succinate are shown in FIG. 11 and FIG. 12, respectively. All data for pretreated cells were normalized for the growth inhibition induced by α-tocopherol succinate plus R1881. While α-tocopherol succinate had no effect on the growth inhibition either by LNM alone or LNM in combination with R1881, it completely reversed the growth inhibitory effect of TG-25 observed in cells pretreated with 1 nM R1881 (FIG. 10). These results unambiguously established TG-25 as a novel drug lead against prostate cancer via an unprecedented mode of action—oxidative activation and episulfornium ion-mediated alkylative DNA cleavage.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Arap et al., (1995) Cancer Res., 55(6):1351–1354.
Arap et al., Science 1998, 279, 377–380.
Bierman et al., (1992) Gene, 116: 43–49.
Caldas et al., (1994) Nat. Genet., 8(1):27–32.
Chen et al., Cancer Res. 2001, 61, 2434–2438.
Cheng et al., (1994) Cancer Res., 54(21):5547–5551.
Cheng et al., (2002) J. Bacteriol. 184, 7013–7024.
Cheng et al., (2003) Proc. Natl. Acad. Sci. USA 100.
Cleary and Sklar, (1985) Proc. Nat'l. Acad. Sci. USA, (21):7439–7443.
Cleary et al., (1986) J. Exp. Med., 164(1):315–320.
Curnis et al., Nature Biotechnol. 2000, 18, 1185–1190.
Curnis, et al., 2002, Cancer Res. 62:867–874.
Ellerby et al., Nature Med. 1999, 5, 1032–1038.
Feuer et al., (1999) J. Natl Cancer Inst., 91(12): 1025–1032.
Froidevaux et al., Biopolymers 2002, 66, 161–183.
Fukuyama et al., (1994) J. Synth. Org. Chem. Japan 52, 888–899.
Gramajo et al., (1991) J. Bacteriol. 173, 6475–6483.
Grim et al., (1994) Gene, 151: 1–10.
Grzegorz et al., 1998, Proc. Nat'l Acad. Sci. USA, 95:11520–11525.
Guilfoile & Hutchinson (1991) Proc. Natl. Acad. Sci. USA, 88: 8553–8557.
Hollstein et al., (1991) Science, 253(5015):49–53.
Hopwood et al., (1985) Genetic manipulation of *Streptomyces*: a laboratory manual., John Innes Foundation: Norwich, UK)
Hopwood et al., (1987) Meth. Enzymol., 153: 116–166.
Hopwood, D. A. and Sherman, D. H. Ann. Rev. Geneet. (1990) 24:37–66.
Huang et al., (1996) Nucl. Acids Res., 24: 4202–4209.
Hussussian et al., (1994) Nat. Genet., 8(1):15–21.
Kamb et al., (1994) Nat. Genet., 8(1):23–26.
Kamb et al., (1994) Science, 2674:436–440.
Kanda et al., (1993) J. Am. Chem. Soc. 115, 8451–8452.
Kanda et al., (1998) Bioorg. Med. Chem. Lett. 8, 909–912.
Kao et al., (1994) Science, 265: 509–512.
Kerr et al., (1972) Br. J. Cancer, 26(4):239–257.
Kwon et al., (2002) Science, 297, 1327–1330.
Liu et al., (2000) Antimicrob. Agents Chemother. 44, 382–392.
Liu et al., (2002) Science, 297, 1170–1173.
Mori et al., (1994) Cancer Res., 54(13):3396–3397.
Motamedi and Hutchinson (1987) Proc. Nat'l. Acad. Sci. USA, 84: 4445–4449.
Nobri et al., (1995) Nature, 368:753–756.
O'Hagan, D. The Polyketide Metabolites (Ellis Horwood Limited, 1991).
Okamoto et al., (1994) Proc. Nat'l. Acad. Sci. USA, 91(23): 11045–11049.
Orlow et al., (1994) Cancer Res, 54(11):2848–2851.
Osoegawa et al., (1998) Genomics, 52: 1–8.
Pieper et al., (1995) J. Am. Chem. Soc., 117: 11373–11374
Pleper et al., (1995) Nature, 378: 263–266.
Sambrook et al., (1989) Molecular Cloning: A Laboratory Manual, Cold Springs Lab., New York.
Serrano et al., (1993) Nature, 366:704–707.
Serrano et al., (1995) Science, 267(5195):249–252.
Shen and Hutchinson, (1994) J. Biol. Chem. 269: 30726–30733
Smith et al., (2000) Antimicrob. Agents Chermother. 44, 1809–1817.
Stutzman-Engwall and Hutchinson (1989) Proc. Nat'l. Acad. Sci. USA, 86: 3135–3139
Tang et al., (2004) Chemistry & Biology, 11:33–45
Tsujimoto and Croce, (1986) Proc. Nat'l. Acad. Sci. USA, 83(14):5214–5218.
U.S. Pat. No. 4,551,433
U.S. Pat. No. 4,551,433
U.S. Patent Application 20030175888.
Vara et al., (1989) J. Bacteriol., 171:5872–5881.
Wang et al., (1998) Proc. Natl. Acad. Sci. U.S.A. 95, 12163–12168.
Wiesmann et al., (1995) Chem. & Biol. 2: 583–589.
Woon et al., (1998) Genomics, 50: 306–316.

What is claimed is:

1. A compound having the structure:

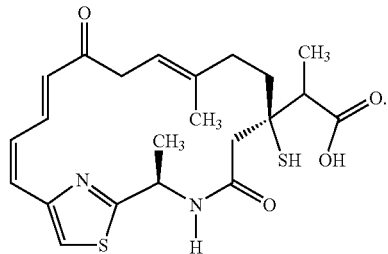

2. A pharmaceutical composition comprising a compound having the structure:

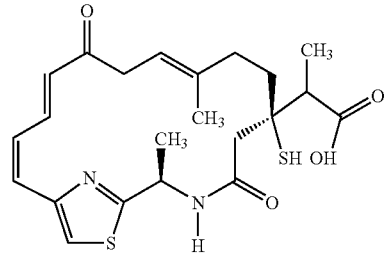

dispersed in a pharmaceutical buffers, diluent or carrier.

* * * * *

UNITED STATES PATENT AND TRADEMARK OFFICE
CERTIFICATE OF CORRECTION

| | | |
|---|---|---|
| PATENT NO. | : 7,345,069 B2 | Page 1 of 1 |
| APPLICATION NO. | : 11/097972 | |
| DATED | : March 18, 2008 | |
| INVENTOR(S) | : Ben Shen | |

It is certified that error appears in the above-identified patent and that said Letters Patent is hereby corrected as shown below:

In claim 2, column 32, line 55, please delete "buffers" and insert --buffer-- therefor.

Signed and Sealed this

Second Day of September, 2008

JON W. DUDAS
*Director of the United States Patent and Trademark Office*